(12) United States Patent
Szu et al.

(10) Patent No.: US 7,527,797 B1
(45) Date of Patent: May 5, 2009

(54) VIBRIO CHOLERAE 0139 CONJUGATE VACCINES

(75) Inventors: Shousun Chen Szu, Bethesda, MD (US); Zuzana Kossaczka, Bethesda, MD (US); John B. Robbins, Chevy Chase, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/363,618

(22) PCT Filed: Sep. 1, 2000

(86) PCT No.: PCT/US00/24119

§ 371 (c)(1),
(2), (4) Date: Sep. 29, 2003

(87) PCT Pub. No.: WO02/20059

PCT Pub. Date: Mar. 14, 2002

(51) Int. Cl.
*A61K 39/00* (2006.01)
*A61K 39/38* (2006.01)
*A61K 39/40* (2006.01)
*A61K 39/385* (2006.01)
*A61K 39/116* (2006.01)
*A61K 39/02* (2006.01)
*A61K 39/106* (2006.01)
*A61K 38/00* (2006.01)
*A61K 38/16* (2006.01)
*A01N 37/18* (2006.01)
*C12P 21/08* (2006.01)
*C08H 1/00* (2006.01)
*C07K 16/00* (2006.01)

(52) U.S. Cl. ............... 424/193.1; 424/184.1; 424/261.1; 424/164.1; 424/194.1; 424/234.1; 424/203.1; 424/236.1; 424/179.1; 424/200.1; 424/183.1; 530/387.1; 530/389.1; 530/403; 514/2; 514/8

(58) Field of Classification Search .................... 514/2; 424/261.1, 184, 193.1, 234.1, 179.1, 183.1; 530/387.1

See application file for complete search history.

(56) References Cited

U.S. PATENT DOCUMENTS

| | | | | |
|---|---|---|---|---|
| 4,496,538 A * | 1/1985 | Gordon | .................... | 424/194.1 |
| 5,204,098 A | 4/1993 | Szu et al. | | |
| 5,653,986 A * | 8/1997 | Morris et al. | ............ | 424/261.1 |
| 5,728,383 A * | 3/1998 | Johnson et al. | .......... | 424/183.1 |
| 5,965,714 A * | 10/1999 | Ryall | ........................ | 530/402 |
| 6,632,437 B1 * | 10/2003 | Schneerson et al. | ...... | 424/193.1 |
| 6,723,323 B1 * | 4/2004 | Gomez et al. | ............ | 424/200.1 |
| 6,756,040 B2 * | 6/2004 | Peetermans et al. | ....... | 424/201.1 |
| 6,818,222 B1 * | 11/2004 | Barchfeld et al. | ........ | 424/236.1 |
| 6,841,160 B2 * | 1/2005 | LaPosta et al. | ........... | 424/250.1 |
| 6,858,211 B1 * | 2/2005 | Szu et al. | ................. | 424/193.1 |
| 7,247,307 B2 * | 7/2007 | Szu et al. | ................. | 424/241.1 |
| 7,261,900 B2 * | 8/2007 | Leppla et al. | ............. | 424/246.1 |
| 7,364,739 B2 * | 4/2008 | Richards et al. | .......... | 424/184.1 |
| 7,384,639 B2 * | 6/2008 | Kende et al. | ............ | 424/197.11 |
| 2003/0068324 A1 * | 4/2003 | Fournier et al. | .......... | 424/184.1 |
| 2004/0170638 A1 * | 9/2004 | Mistretta et al. | ......... | 424/184.1 |
| 2004/0258702 A1 * | 12/2004 | Blonder et al. | ........... | 424/184.1 |
| 2007/0166315 A1 * | 7/2007 | Szu et al. | ................. | 424/164.1 |
| 2008/0260773 A1 * | 10/2008 | Del Giudice et al. | ... | 424/196.11 |

FOREIGN PATENT DOCUMENTS

| | | |
|---|---|---|
| WO | WO 91 01146 A | 2/1991 |
| WO | WO 95 15178 A | 6/1995 |
| WO | WO 00 48638 A | 8/2000 |

OTHER PUBLICATIONS

Boutonnier et al, Infection and Immunity, May 2001, 69/5:3488-3493.*
Chatterjee et al, BBA, 2003, 1639:65-79.*
Ramamurthy et al, Microbes and Infection, 2003, 5:329-344.*
Eko et al, Vaccine, 2003, 21:3663-3674.*
Szu et al, Exptal. Med., 1987, 166:1510-1524.*
Johnson et al, JBC, 1994, 269/6:4349-4354.*
Granoff et al, J. Clin. Invest., 1993, 91:788-796.*
Barbieri et al, Infection and Immunity, 1992, 60/12:5071-5077.*
Peeters et al, Infection and Immunity, 1991, 59/10:3504-3510.*
Ravenscroft et al, Dev. Biol. (Basel), 2000, 103:35-47 abstract only.*

(Continued)

Primary Examiner—N. M Minnifield
(74) Attorney, Agent, or Firm—Klarquist Sparkman, LLP

(57) ABSTRACT

The invention pertains to conjugates of the capsular polysaccharide of *Vibrio cholerae* O139, or a structurally and/or immunologically related oligo- or poly-saccharide, and a carrier. These conjugates are useful as pharmaceutical compositions and/or vaccines to induce serum antibodies which have bactericidal (vibriocidal) activity against *V. cholerae*, in particular *V. cholerae* O139, and are useful to prevent, treat and/or reduce the severity of disease caused by *V. cholerae* infection, such as cholera. The present invention also relates to diagnostic tests for *V. cholerae* infection, and/or cholera caused by *V. cholerae* infection, using one or more of the oligo- or poly-saccharide-carrier conjugates or antibodies described above.

8 Claims, 4 Drawing Sheets

OTHER PUBLICATIONS

Figure 1:
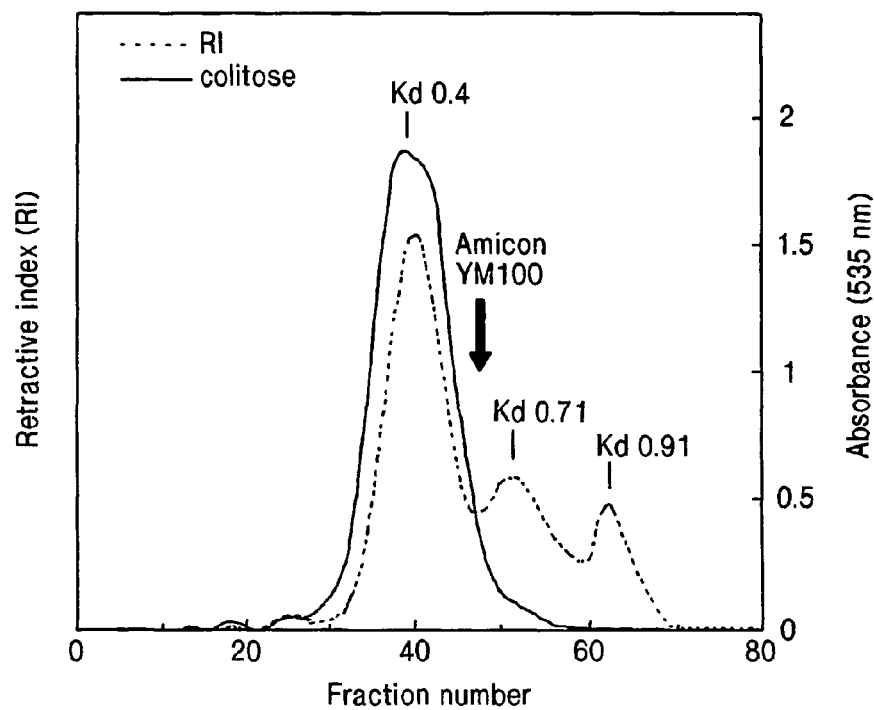

Porro et al, J. Infect Dis., 1980, 142/5:716-724 abstract only.*
Porro et al, Mol. Immunol., 1985, 22/8:907-919 abstract only.*
Cryz et al, Infection and Immunity, 1980, 30/3:835-846.*
Bigio et al, FEBS Letters, 1987, 218/2:271-276.*
Bondre et al., "Evaluation of Different Subcellular Fractions of *Vibrio cholerae* O139 in Protection to Challenge in Experimental Cholera," *FEMS Immunol. Med. Microbiol. 19*:323-329 (1998).
Favre et al., "Construction Characterization of a Potential Live Oral Carrier-Based Vaccine against *Vibrio cholerae* O139," *Infect. and Immun. 64*:3565-3570 (1996).
Gunawardena et al., "Conformation of a Rigid Tetrasaccharide Epitope in the Capsular Polysaccharide of *Vibrio cholerae* O139," *Biochem. 38*:12062-12071 (1999).
Gupta et al., "Phase 1 Evaluation of *Vibrio cholerae* O1, Serotype Inaba, Polysaccharide- Cholera Toxin Conjugates in Adult Volunteers," *Infect. Immun. 66*:3095-3099 (1998).
Johnson et al., "Capsular Polysaccharide-Protein Conjugate Vaccines Against *Vibrio cholerae* O139 Bengal," *Bull. Inst. Pasteur 93*:285-290 (1995).
Jonson et al., "Immune Mechanisms and Protective Antigens of *Vibrio cholerae* Serogroup O139 as a Basis for Vaccine Development," *Infect. Immun. 64*:3778-3785 (1996).
Kossaczka et al., "*Vibrio cholerae* O139 Conjugate Vaccines: Synthesis and Immunogenicity of *V. cholerae* O139 Capsular Polysaccharide Conjugates With Recombinan Diphtheria Toxin Mutant in Mice," *Infect. Immun.* 68:5037-5043 (2000).
Kossaczka et al., "Evaluation of Synthetic Schemes to Prepare Immunogenic Conjugates of *Vibrio cholerae* O139 Capsular Polysaccharide with Chicken Serum Albumin," *Glycoconjugate Journal 17*:425-433 (2000).
Oscarson et al., "Synthesis of Colitose-Containing Oligosaccharide Structures Found in Polysaccharides from *Vibrio cholerae* O139 Synonym Bengal Using Thioglycoside Donors," *Carbohydr. Res. 299*:159-164 (1997).
Preston et al., "Preliminary Structure Determination of the Capsular Polysaccharide of *Vibrio cholerae* O139 Bengal A11837," *J. Bacteriol. 177*:835-838 (1995).
Sengupta et al., "Antibody Against the Capsule of *Vibrio cholerae* O139 Protects Against Experimental Challenge," *Infect. Immun.* 64:343-345 (1996).
Szu et al., in *Vibrio cholerae and Cholera*, Wachsmuth et al. (eds.), pp. 381-394, American Society for Microbiology, Washington, D.C. (1994).

* cited by examiner

VIBRIO CHOLERAE 0139 CONJUGATE VACCINES

PRIORITY CLAIM

This is a § 371 U.S. national stage of PCT/US00/24119, filed Sep. 1, 2000, which was published in English under PCT Article 21(2).

FIELD OF THE INVENTION

This invention relates to compositions and methods for eliciting an immunogenic response in mammals, including responses which provide protection against, or reduce the severity of, bacterial infections. More particularly it relates to conjugates of the capsular polysaccharide of *Vibrio cholerae* O139, or a structurally and/or immunologically related oligo- or poly-saccharide, and a carrier. These conjugates are useful as pharmaceutical compositions and/or vaccines to induce serum antibodies which have bactericidal (vibriocidal) activity against *V. cholerae*, in particular *V. cholerae* O139, and are useful to prevent, treat and/or reduce the severity of disease caused by *V. cholerae* infection, such as cholera.

The present invention also relates to diagnostic tests for *V. cholerae* infection, and/or cholera caused by *V. cholerae* infection, using one or more of the oligo- or poly-saccharide-carrier conjugates, or antibodies described above.

The present invention also relates to methods of making oligo- or poly-saccharide carrier conjugates using CDAP to activate carboxylic acids on the carbohydrate. The present invention also relates to methods of separating *V. cholerae* CPS from contaminating smaller molecules by means of diafiltration.

Abbreviations used: LPS: lipopolysaccharide; CPS: capsular polysaccharide; O-SP: O-specific polysaccharide; DT: diphtheria toxin; HSA: human serum albumin; DCC: dicyclohexyl carbodiimide; EDC: 1-ethyl-3-(3-dimethylaminopropyl)carbodiimide; CDAP: 1-cyano-4-dimethylaminopyridinium tetrafluoroborate; ADH: adipic acid dihydrazide; rDT: recombinant diphtheria toxin mutant CRMH21G.

BACKGROUND OF THE INVENTION

The most successful of all carbohydrate pharmaceuticals so far have been the carbohydrate-based antibacterial vaccines [48]. The basis of using carbohydrates as vaccine components is that the capsular polysaccharides and the O-specific polysaccharides on the surface of pathogenic bacteria are both protective antigens and essential virulence factors. The first saccharide-based vaccines contained capsular polysaccharides of *Pneumococci*: in the United States a 14-valent vaccine was licensed in 1978 followed by a 23-valent vaccine in 1983. Other capsular polysaccharides licensed for human use include a tetravalent meningococcal vaccine and the Vi polysaccharide of *Salmonella typhi* for typhoid fever. The inability of most polysaccharides to elicit protective levels of anti-carbohydrate antibodies in infants and adults with weakened immune systems can be overcome by their covalent attachment to proteins that confer T-cell dependent properties [49]. This principles has led to the construction of vaccines against *Haemophilus influenzae* b (Hib) [37] and in countries where these vaccines are routinely used, meningitis and other diseases caused by Hib have been virtually eliminated [50]. Extension of the conjugate technology to the O-specific polysaccharides of Gram-negative bacteria has provided a new generation of glycoconjugate vaccines that are undergoing various phases of clinical trials [51].

Cholera remains an important public health problem. The long-term control of cholera depends on good personal hygiene, uncontaminated water supply and appropriate sewage disposal. However, the improvement of hygiene is a distant goal for many countries. Thus the availability of an effective cholera vaccine is important for the prevention of cholera in these countries. Research on new cholera vaccines has mainly focused on oral formulations that stimulate the mucosal secretory immune system. Two oral cholera vaccines have been experimented with on large scale in humans.

The first vaccine, containing inactivated bacterial cells and the B-subunit of cholera toxin, was tested in Bangladesh from 1985 to 1989. This vaccine, according to the WHO, may prove useful in the stable phase of refugee/displaced person crises, especially when given preventively. The second vaccine is a live attenuated vaccine containing the genetically manipulated *V. cholerae* O1 strain CVD 103-HgR. Despite its efficacy in adult volunteers, results of a large-scale field trial carried-out in Indonesia for 4 years have shown a surprisingly low protection. Moreover, one of the safety concerns associated with live cholera vaccine is a possible horizontal gene transfer and recombination event leading to reversion to virulence. [52]

More recently, conjugates of *V. cholerae* O1 lipopolysaccharide with cholera toxin variants were prepared with an adipic acid dihydrazide linker. In Phase I studies, these conjugates elicited vibriocidal antibodies in human volunteers, with IgM levels comparable to, and IgG levels superior to, the Ig levels elicited by a cellular vaccine [10, 36, 38, 39]. Conjugation of the *V. cholerae* O139 CPS to tetanus toxoid, and inoculation of mice with the conjugate, has also been described by Morris et al. in U.S. Pat. No. 5,653,986.

Until 1992, *V. cholerae* serogroup O1 was recognized as the sole cause of cholera epidemics, whereas the non-O1 serogroups were associated with sporadic cases of gastroenteritis and extra-intestinal infections. In late 1992, the etiological agent of a massive cholera epidemic was identified as non-O1 *V. cholerae* serogroup O139. [53] This was the first reported instance of an encapsulated strain that caused epidemic cholera. [11]

The surface polysaccharide of *V. cholerae* O1 is a lipopolysaccharide (LPS), whereas *V. cholerae* O139, in contrast, has a capsular polysaccharide (CPS) composed of a hexasaccharide repeating unit, containing a trisaccharide backbone and two branches [3, 4, 8, 11, 16, 17, 19, 26, 28, 30, 31, 35, 38, 42, 43, 45]. The repeating unit contains two negatively charged groups, a galacturonic acid carboxyl group and a cyclic phosphate diester. This repeating unit is incorporated into the *V. Cholerae* O139 lipopolysaccharide as well as the capsular polysaccharide, and it is possible that the *V. cholerae* O139 CPS is in fact a very high molecular weight LPS.

Passive immunization of mice with antiserum to the *V. cholerae* O139 capsular polysaccharide has been shown to protect against variants of *V. cholerae* O139, and it has been proposed that conjugates of the *V. cholerae* O139 capsular polysaccharide with cholera toxin or toxoid might be "worthy of further study" [38]. A potential live oral vaccine, comprising a non-pathogenic deletion mutant of *V. cholerae* engineered to express the *V. cholerae* O139 capsular polysaccharide and core-linked O-polysaccharide, has been described [62]. The vaccine elicited anti-CPS antibodies in rabbits, but neither animal protection studies nor clinical results have been reported to date.

It has been proposed that a critical level of serum IgG to the surface polysaccharides of *V. cholerae* O1 and *V. cholerae* O139 confers serotype-specific immunity to cholera [3, 7, 17, 24, 25, 28, 29-32, 38, 39, 43, 44]. It has also been proposed that the level of IgG, rather than the total level of vibriocidal antibodies may correlate more accurately with protection against cholera, because (1) synthesis of IgG is predictive of long-lived immunity, probably reflecting induction of T-helper cells to the antigen-specific B-cells, and (2) IgG antibodies penetrate into the extracellular spaces and interior of the small intestine more effectively than IgM. IgG directed to the O-specific polysaccharide of *V. cholerae* O1 or *V. cholerae* O139 could confer protective immunity to cholera by inactivating the inoculum on the intestinal mucosal surface.

Currently, vibriocidal antibody titers induced by vaccines are regarded as being predictive of therapeutic utility, at least for vaccines that have passed regulatory review: vibriocidal titer is the only serologic assay required by the U.S. Food and Drug Administration for licensure of new cholera vaccine lots. [61].

Previously described conjugates of the *V. cholerae* O139 CPS have not demonstrated the induction of adequate levels of IgG antibodies to provide reliable vaccines; accordingly there still remains a need for improved conjugates.

SUMMARY OF THE INVENTION

It is an object of the present invention to provide conjugates comprising the capsular polysaccharide of *V. cholerae* O139 and a carrier. It is also an object of the invention to provide conjugates comprising oligo- or poly-saccharides which are structurally related and/or antigenically similar to the capsular polysaccharide of *V. cholerae* O139. Preferably, these oligo- or poly-saccharides of the invention are antigenically similar to the capsular polysaccharide of *V. cholerae* O139. These oligo- or poly-saccharide conjugates are immunogenic and elicit serum antibodies that are bactericidal against *V. cholerae*, in particular *V. cholerae* O139, and are useful in the prevention, treatment, and reduction in severity of disease caused by *V. cholerae*. These oligo- or poly-saccharide conjugates, and the antibodies which they elicit, are also useful for studying *V. cholerae*, in particular *V. cholerae* O139, in vitro, and for studying its products in patients.

It is yet another object of the present invention to provide antibodies which have vibriocidal activity against *V. cholerae*, in particular *V. cholerae* O139, and which react with, or bind to, the capsular polysaccharide of *V. cholerae* O139, wherein the antibodies are elicited by immunization with a carrier-conjugate comprising the natural *V. cholerae* capsular polysaccharide, or a structurally and/or immunologically related natural, synthetic or semi-synthetic oligo- or polysaccharide, preferably a semi-synthetic or synthetic oligo- or poly-saccharide comprising one or more, preferably four or more, repeating hexasaccharide units of *V. cholerae* O139 capsular polysaccharide.

It is yet another object of the present invention to provide carrier-conjugates which are useful as pharmacuetical compositions and/or vaccines to prevent, treat and/or ameliorate diseases, such as cholera, caused by *V. cholerae*, in particular *V. cholerae* O139.

It is yet another object of the present invention to prepare antibodies for the prevention, treatment or amelioration of cholera. Antibodies elicited by the carrier conjugates of the invention are useful in providing passive protection to an individual exposed to *V. cholerae*, in particular *V. cholerae* O139, to prevent, treat, or ameliorate infection and disease caused by the microorganism.

It is yet another object of the present invention to provide diagnostic tests and/or kits for disease caused by *V. cholerae*, in particular *V. cholerae* O139, using one or more of the carrier-conjugates, and/or antibodies, of the present invention.

It is yet another object of the present invention to provide a method for synthesizing a conjugate vaccine comprising *V. cholerae* O139 capsular polysaccharide covalently linked to a polypeptide, such as diphtheria toxin (DT) derivative which has a lower toxicity than DT and is suitable for clinical use.

Methods are also provided to conjugate the natural, semi-synthetic, or synthetic oligo- or poly-saccharides of the invention with a carrier.

Methods are also provided for separating CPS from contaminating smaller molecules by diafiltration.

BRIEF DESCRIPTION OF THE DRAWINGS

FIG. 1. SEPHAROSE™ (cross-linked agarose) CL-4B gel filtration profile of the unfractionated *V. cholerae* O139 capsular polysaccharide (CPS). Refractive index (RI) response (broken line); Colitose-containing fractions (solid line); the arrow indicates the point of separation between the retentate and filtrate by diafiltration (Amicon YM100) of the unfractionated CPS; Distribution coefficients (Kd) are depicted above each peak.

FIG. 2. $^{13}C$ NMR spectrum of *V. cholerae* O139 capsular polysaccharide. Legend: $^{13}C$ NMR spectrum of the CPS (50 mg/ml $D_2O$) was measured using Varian XL3000 spectrometer by averaging 50,000 scans with a 10-s decay between acquisition and 10 μs 90° pulse. Prior to Fourier transformation, a 5-Hz line broadening was applied and zero-filled to 32,000 datum points.

FIG. 3. SEPHAROSE™ (cross-linked agarose) CL-4B gel filtration profiles of *V. cholerae* O139 CPS conjugates with rDT. Representative chromatograph of the $CPS_{AH}$-rDT conjugates (A) prepared by EDC-mediated synthesis or of CPS-$rDT_{AH}$ conjugates (B) prepared by CDAP-mediated synthesis. Legend: Polysaccharide (■) and protein (○).

FIG. 4. Double immunodiffusion of *V. cholerae* O139 conjugates with murine hyperimmune cholera O139 and equine diphtheria toxin antisera: (A) representative pattern for $CPS_{AH}$-rDT conjugates and (B) representative pattern for CPS-$rDT_{AH}$ conjugates. Legend: 1 murine hyperimmune cholera O139 antiserum, 3 μl; 2 equine diphtheria toxin antiserum, 5 μl, 3 conjugate (PS: 1-4 μg; PR: 1-8 μg).

FIG. 5. Structure of the repeating hexasaccharide unit of the *V. cholerae* O139 capsular polysaccharide.

DETAILED DESCRIPTION OF THE INVENTION

In preliminary studies the present inventors found that *V. cholerae* CPS does not elicit serum antibodies after three injections in mice. To improve its immunogenicity, CPS was covalently bound by a variety of different synthetic methods to chicken serum albumin, a model protein. The resultant conjugates induced serum anti-CPS IgG in mice with vibriocidal activity. CPS was then covalently bound by several methods to the diphtheria toxin mutant CRMH21G.

The recombinant diphtheria toxin mutant CRMH21G was prepared by replacing histidine 21 with glycine in the A-chain of diphtheria toxin [15]. This mutant protein has a $1\times10^{-4}$ lower toxicity than diphtheria toxin (DT) and is suitable for clinical use. The two synthetic schemes found most successful with the chicken albumin, involving 1-ethyl-3-(3-dimethylaminopropyl)carbodiimide (EDC) and 1-cyano-4-dimethylaminopyridinium tetrafluoroborate (CDAP) as activating agents, were adapted to prepare 4 conjugates of *V.*

*cholerae* O139 CPS with the recombinant diphtheria toxin mutant, CRMH21G. Adipic acid dihydrazide was used as a linker.

When injected subcutaneously into young outbred mice in a clinically relevant dose and schedule, these conjugates elicited very high levels of serum CPS antibodies of IgG and IgM classes, with vibriocidal activity to strains of capsulated *V. cholerae* O139. Treatment of these sera with 2-mercaptoethanol (2-ME) reduced, but did not eliminate, their vibriocidal activity. These results indicate that the conjugates elicited IgG with vibriocidal activity. The conjugates also elicited high levels of serum diphtheria toxin IgG.

Convalescent sera from 20 cholera patients infected with *V. cholerae* O139 had vibriocidal titers ranging from 100 to 3200. Absorption with the CPS reduced vibriocidal titer of all sera to $\leq 50$. Treatment with 2-ME reduced the titers of 17 of the 20 to $\leq 50$. These data show that, similar to infection with *V. cholerae* O1, infection with *V. cholerae* O139 induces vibriocidal antibodies specific to the surface polysaccharide of this bacterium (CPS) that are mostly of IgM class.

These results clearly indicate that the conjugates of the invention are capable of inducing anti-*V. cholerae* CPS antibodies having desirable properties. Based on these data, clinical trials of the *V. cholerae* O139 CPS-rDT conjugates of this invention are planned.

Accordingly, one object of the invention is a vaccine that will induce antibodies with vibriocidal activity against *V. cholerae*, in particular *V. cholerae* O139. These antibodies may be obtained by parenteral administration of a vaccine containing natural *V. cholerae* CPS, or a structurally and/or immunologically related natural, synthetic or semi-synthetic oligo- or poly-saccharide, conjugated to a carrier. The oligo- or poly-saccharide, as a natural, synthetic, or semi-synthetic product, may be bound to both a carrier saccharide and a non-toxic non-host protein carrier or directly to a non-toxic non-host protein carrier to form a conjugate. The present invention also encompasses mixtures of the oligo- or poly-saccharides and conjugates thereof.

The vaccine compositions of the invention will preferably induce protective levels of anti-*V. cholerae* O139 antibodies, so as to render the recipient immune to infection by *V. cholerae* O139, or resistant to cholera caused by *V. cholerae* O139, after one or more doses of vaccine. The levels of antibodies induced by the vaccine will preferably result in vibriocidal titers of greater than 800, more preferably greater than 1600, and most preferably greater than 3200, when measured against *V. cholerae* O139 SPH1168.

The saccharide-based vaccine is intended for active immunization for prevention of cholera, but may also be used for preparation of immune antibodies as a therapy. This CPS-based vaccine is designed to confer specific preventative immunity to infection with *V. cholerae*, in particular *V. cholerae* O139, and to induce antibodies specific to *V. cholerae* O139 CPS for prevention and/or treatment of cholera.

The conjugates of the invention, as well as the antibodies thereto, will be useful in increasing resistance to, preventing, ameliorating, and/or treating disease, such as cholera, caused by *V. cholerae*, in particular *V. cholerae* O139, in humans.

Specifically, it is expected that conjugates of *V. cholerae* O139 CPS will elicit serum antibodies specific to *V. cholerae* O139 CPS, which should induce complement-dependent killing of *V. cholerae* O139. It is also expected that these serum antibodies specific to *V. cholerae* O139 CPS will protect against *V. cholerae* O139, infection in mammals, including humans.

A number of primary uses for the compounds of this invention are envisioned. The invention is intended to be included in the routine immunization schedule of infants and children living in areas where cholera is endemic, and in individuals at risk for cholera, such as travelers to areas where cholera is endemic. It is also intended to be used for intervention in epidemics caused by *V. cholerae* O139. Additionally, it is planned to be used for a multivalent vaccine for *V. cholerae* and other enteric pathogens for routine immunization in infants.

The invention may also be used to prepare antibodies with vibriocidal activity against *V. cholerae*, in particular *V. cholerae* O139, for therapy of cholera. The invention may also be used to provide a diagnostic test for cholera caused by *V. cholerae*, in particular *V. cholerae* O139.

The conjugates of the invention are also expected to be capable of inducing anti-DT antibodies which may prevent, lessen or attenuate the severity, extent or duration of an infection by *Corynebacterium diptheriae*.

Definitions:

"Oligosaccharide" as defined herein is a carbohydrate containing up to twelve monosaccharide units linked together. A "polysaccharide" as defined herein is a carbohydrate containing more than twelve monosaccharide subunits linked together.

As used herein, "natural" refers to a native or naturally occurring oligo- or poly-saccharide which has been isolated from an organism, e.g., *V. cholerae* O139, and "semi-synthetic" refers to a native or naturally occurring polysaccharide that has been structurally altered. Such structural alterations are any alterations that render the modified polysaccharide antigenically similar to the capsular polysaccharide of *V. cholerae*, in particular *V. cholerae* O139. Preferably, the structural alterations substantially approximate the structure of an antigenic determinant of the capsular polysaccharide of *V. cholerae* O139.

In other words, a modified oligo- or poly-saccharide of this invention is characterized by its ability to immunologically mimic the capsular poly-saccharide of *V. cholerae* O139, in particular *V. cholerae* O139. Such a modified oligo- or poly-saccharide is useful herein as a component in an inoculum for producing antibodies that preferably immunoreact with, or bind to, the capsular polysaccharide of *V. cholerae* O139.

As used herein, the term "immunoreact" means specific binding between an antigenic determinant-containing molecule and a molecule containing an antibody combining site such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$ and F(v), as well as chimeric antibody molecules.

As used herein, the phrase "immunologically similar to" or "immunologically mimic" refers to the ability of an oligo- or poly-saccharide of the invention to immunoreact with, or bind to, an antibody of the present invention that recognizes and binds to a native antigenic determinant on the capsular polysaccharide of *V. cholerae* O139.

It should be understood that an oligo- or poly-saccharide of the invention need not be structurally identical to the capsular polysaccharide of *V. cholerae* O139 so long as it is able to elicit antibodies that immunoreact with, or bind to, the capsular polysaccharide of *V. cholerae* O139.

An oligo- or poly-saccharide of the invention includes any substituted analog, fragment or chemical derivative (either natural or synthetic) of the capsular polysaccharide of *V. cholerae* O139 so long as the oligo- or poly-saccharide is capable of reacting with antibodies that immunoreact with the capsular polysaccharide of *V. cholerae* O139. Therefore, an oligo- or poly-saccharide can be subject to various changes that provide for certain advantages in its use. For example, it has been observed that loss of the colitose residues from the capsular polysaccharide abolishes antigenicity, and therefore at least one important antigenic determinant of *V. cholerae* O139 CPS comprises or consists of one or more colitose residues. Synthetic portions of *V. cholerae* O139 capsular polysaccharide, and analogs thereof, may be prepared by those skilled in the art of carbohydrate synthesis [see, e.g., reference 46].

The terms "substitute", "substituted" and "substitution" include the use of a chemically derivatized residue in place of a non-derivatized residue provided that the resulting modified oligo- or poly-saccharide displays the requisite immunological activity.

"Chemical derivative" refers to a modified oligo- or poly-saccharide having one or more residues chemically derivatized by reaction of a functional side group. For example, one or more hydroxyl groups of the oligo- or poly-saccharide may be reduced, oxidized, esterified, or etherified; or one or more acetamido groups may be hydrolyzed or replaced with other carboxamido or ureido groups, and suitably disposed pairs of hydroxyl groups may be converted into cyclic phosphate diesters. Such transformations are well-known and within the abilities of those skilled in the art of carbohydrate chemistry. Additional residues may also be added for the purpose of providing a "linker" by which the modified oligo- or poly-saccharide of this invention can be conveniently affixed to a label or solid matrix or carrier. Suitable residues for providing linkers may contain amino, carboxyl, or sulfhydryl groups, for example. Labels, solid matrices and carriers that can be used with the oligo- or poly-saccharide of this invention are described hereinbelow.

Polymeric Carriers

Carriers are chosen to increase the immunogenicity of the oligo- or poly-saccharide and/or to raise antibodies against the carrier which are medically beneficial. Carriers that fulfill these criteria are described in the art (see, e.g., references 54-59). Polymeric carriers can be a natural or a synthetic material containing one or more primary and/or secondary amino groups, azido groups, or carboxyl groups. The carrier can be water soluble or insoluble.

Examples of water soluble peptide carriers include, but are not limited to, natural or synthetic peptides or proteins from bacteria or virus, e.g., tetanus toxin/toxoid, diphtheria toxin/toxoid, *Pseudomonas aeruginosa* exotoxin/toxoid/protein, pertussis toxin/toxoid, *Clostridium perfringens* exotoxins/toxoid, and hepatitis B surface antigen and core antigen. Mutants of these peptides, derived for example by amino acid substitution or deletion, may also be employed as carriers. Toxins, toxoids and mutants of toxins having reduced toxicity are preferred carriers.

Polysaccharide carriers include, but are not limited to, capsular polysaccharides from microorganisms such as the Vi capsular polysaccharide from *S. typhi*, which contains carboxyl groups and which is described in U.S. Pat. No. 5,204,098, incorporated by reference herein; *Pneumococcus* group 12 (12F and 12A) polysaccharides, which contain a terminal galactose: and *Haemophilus influenzae* type d polysaccharide, which contains an amino terminal; as well as plant, fruit, or synthetic oligo- or polysaccharides which are immunologically similar to such capsular polysaccharides, such as pectin, D-galacturonan, oligogalacturonate, or polygalacturonate, which are described in U.S. Pat. No. 5,738,855, incorporated by reference herein.

Example of water insoluble carriers include, but are not limited to, aminoalkyl-SEPHAROSE™ (cross-linked agarose), e.g., aminopropyl or aminohexyl SEPHAROSE™ (cross-linked agarose), and aminopropyl glass and the like. Other carriers may be used when an amino or carboxyl group is added through covalent linkage with a linker molecule.

Methods for Attaching Polymeric Carriers

The oligo- or poly-saccharides of the invention may be bound to both a carrier saccharide and a non-toxic non-host protein carrier or directly to a non-toxic non-host protein carrier to form a conjugate.

When the oligo- or poly-saccharide of the invention is bound to both a carrier saccharide and a non-toxic non-host protein carrier, it may be bound first to the carrier saccharide, then the saccharide-carrier conjugate can be bound to the non-toxic non-host protein carrier. The complex compound would properly be described as a semi-synthetic complex molecule with three distinct domains and origins. This complex compound would first contain an oligo- or poly-saccharide bound to the carrier polysaccharide and then the two-domain saccharide bound to a protein. Alternatively, the oligo- or poly-saccharide of the invention may be bound to both a carrier saccharide and a non-toxic non-host protein carrier simultaneously.

Methods for binding a polysaccharide to a protein, with or without a linking molecule, are well known in the art. See for example reference [60], where 3 different methods for conjugating *Shigella* O-SP to tetanus toxoid are exemplified. See also reference [22], which describes methods for conjugating *S. typhi* Vi and adipic hydrazide-derivatized proteins. In U.S. Pat. No. 5,204,098 and U.S. Pat. No. 5,738,855, it is taught that an oligo- or poly-saccharide containing at least one carboxyl group, through carbodiimide condensation, may be thiolated with cystamine, or aminated with adipic dihydrazide, diaminoesters, ethylenediamine and the like. Groups which could be introduced by this method, or by other methods known in the art, include thiols, hydrazides, amines and carboxylic acids. Both the thiolated and the aminated intermediates are stable, may be freeze dried, and may be stored at low temperature. The thiolated intermediate may be reduced and covalently linked to a polymeric carrier containing a sulfhydryl group, such as a 2-pyridyldithio group. The aminated intermediate may be covalently linked to a polymeric carrier containing a carboxyl group through carbodiimide condensation.

The oligo- or poly-saccharide can be covalently bound to a carrier with or without a linking molecule. To conjugate without a linker, for example, a carboxyl-group-containing oligo- or poly-saccharide and an amino-group-containing carrier are mixed in the presence of a carboxyl activating agent, such as for example a carbodiimide, in a choice of solvent appropriate for both the oligo- or poly-saccharide and the carrier, as is known in the art [58]. The oligo- or poly-saccharide is preferably conjugated to a carrier using a linking molecule. A linker or crosslinking agent, as used in the present invention, is preferably a small linear molecule having a molecular weight of approximately <500 and is non-pyrogenic and non-toxic in the final product form (54-59). To conjugate with a linker or crosslinking agent, either or both of the oligo- or poly-saccharide and the carrier may be covalently bound to a linker first. The linkers or crosslinking agents are homobifunctional or heterobifunctional molecules, e.g., adipic dihydrazide, ethylene diamine, cystamine, N-succinimidyl 3-(2- pyridyldithio)propionate (SPDP), N-succinimidyl-N-(2-iodoacetyl)-β-alaninate-propionate (SIAP), succinimidyl 4-(N-maleimido-methyl)cyclohexane-1-carboxylate (SMCC), 3,3'-dithiodipropionic acid, and the like. Dicarboxylic acid dihydrazides are preferred. In the examples presented herein, the linker is adipic acid dihydrazide, attached via hydrazide linkages to carboxyl groups of the oligosaccharide and the polypeptide. Similar results would be expected with any two- to ten-carbon dihydrazide linker. Other amino-containing linkers may similarly be bound to carboxyl groups of the oligo- or poly-saccharide or the carrier through carbodiimide condensation. Carboxylic acid containing linkers may be bound to the amino groups of the carrier by means of carboxyl activating reagents (e.g., carbodiimide condensation) or via N-hydroxysuccinimidyl esters or other reactive derivatives. The unbound materials are removed by physicochemical methods such as gel filtration or ion exchange column depending on the materials to be separated. The final conjugate consists of the oligo- or poly-saccharide and the carrier bound through a linker.

In the present invention, attachment of the *V. cholerae* capsular polysaccharide to a protein carrier is preferably accomplished by first coupling a dicarboxylic acid dihydrazide linker to the CPS, by treatment with a carboxyl activating reagent, such as a water-soluble carbodiimide (e.g., 1-ethyl-3-(3-dimethylaminopropyl)carbodiimide (DEC) or 1-ethyl-3-(3-dimethylaminopropyl)carbodiimide methiodide (EDC)), but preferably through one or more hydroxyl groups, using for example 1-cyano-4-dimethylaminopyridinium tetrafluoroborate (CDAP), to produce a hydrazide-functionalized polysaccharide. Adipic acid dihydrazide is a particularly preferred linker, but conjugates employing other linkers, such as the dihydrazides of succinic, suberic, and sebacic acids, are contemplated to be within the scope of the invention. The linker-functionalized *V. cholerae* capsular polysaccharide ($CPS_{AH}$) is then coupled to the carrier protein, preferably with a water-soluble carbodiimide, most preferably EDC. In an alternative embodiment, the carrier protein (rDT) is first coupled to the linker, again using a water-soluble carbodiimide, preferably EDC, and the linker-functionalized carrier ($rDT_{AH}$) is then coupled to the CPS with a carboxyl activating reagent, or preferably by hydroxyl coupling using for example CDAP. For preparation of the conjugates of this invention, activation of CPS for coupling (with linker or with $rDT_{AH}$) is preferably carried out with CDAP, and activation of rDT (for coupling with linker or with $CPS_{AH}$) is most preferably carried out with EDC.

Dosage for Vaccination

The present inoculum contains an effective, immunogenic amount of oligo- or poly-saccharide carrier conjugate of this invention. The effective amount of oligo- or poly-saccharide carrier conjugate per unit dose sufficient to induce an immune response to *V. cholerae*, in particular *V. cholerae* O139, depends, among other things, on the species of mammal inoculated, the body weight of the mammal and the chosen inoculation regimen as is well known in the art. Inocula typically contain oligo- or poly-saccharide carrier conjugates with concentrations of oligo- or poly-saccharide of about 1 micrograms to about 100 milligrams per inoculation (dose), preferably about 3 micrograms to about 100 micrograms per dose, most preferably about 5 micrograms to about 50 micrograms, and most preferably about 5 micrograms to about 25 micrograms per dose.

The term "unit dose" as it pertains to the inocula refers to physically discrete units suitable as unitary dosages for mammals, each unit containing a predetermined quantity of active material (oligo- or poly-saccharide conjugate) calculated to produce the desired immunogenic effect in association with the required diluent.

Inocula are typically prepared as a solution in a physiologically tolerable (acceptable) diluent such as water, saline or phosphate-buffered saline or other physiologically tolerable diluent to form an aqueous pharmaceutical composition.

The route of inoculation may be intramuscular, subcutaneous and the like, which results in eliciting antibodies protective against *V. cholerae*, in particular *V. cholerae* O139. The dose is administered at least once. In order to increase the antibody level, a second or booster dose may be administered approximately 4 to 6 weeks after the initial injection. Subsequent doses may be administered as indicated.

Adjuvants, such as aluminum hydroxide, QS-21, TITER-MAX™ (immunoadjuvant) (CytRx Corp., Norcross Ga.), Freund's complete adjuvant, Freund's incomplete adjuvant, interleukin-2, thymosin, and the like, may also be included in the compositions.

Antibodies

An antibody of the present invention in one embodiment is characterized as comprising antibody molecules that immunoreact with the capsular polysaccharide of *V. cholerae* O139.

An antibody of the present invention is typically produced by immunizing a mammal with an immunogen or vaccine containing a molecular conjugate of the *V. cholerae* O139 capsular polysaccharide (or a structurally and/or immunologically related molecule) in an amount sufficient to induce, in the mammal, antibody molecules having immunospecificity for the capsular polysaccharide of *V. cholerae* O139. The capsular polysaccharide or related molecule is preferably conjugated to a carrier. The antibody molecules may be collected from the mammal and isolated by methods known in the art.

For administration to humans, human or humanized monoclonal antibodies are preferred, including those made by phage display technology or by non-human mammals engineered to produce human antibodies.

The antibody molecules of the present invention may be polyclonal or monoclonal. Monoclonal antibodies may be produced by methods known in the art. Portions of immunoglobulin molecules, such as Fabs, may also be produced by methods known in the art.

The antibody of the present invention may be contained in blood plasma, serum, hybridoma supernatants and the like. Alternatively, the antibody of the present invention is isolated to the extent desired by well known techniques such as, for example, ion chromatography or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection.

The antibodies of the present invention have a number of diagnostic and therapeutic uses. The antibodies can be used as an in vitro diagnostic agent to test for the presence of *V. cholerae*, in particular *V. cholerae* O139, in biological samples in standard immunoassay protocols. Such assays include, but are not limited to, agglutination assays, radioimmunoassays, enzyme-linked immunosorbent assays, fluorescence assays, Western blots and the like. In one such assay, for example, the biological sample is contacted to antibodies of the present invention and a labeled second antibody is used to detect the presence of *V. cholerae*, in particular *V. cholerae* O139, or the capsular polysaccharide antigen of *V. cholerae*, in particular *V. cholerae* O139, to which the antibodies are bound.

Such assays may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabelled antibody are utilized), as well as other formats described in the art.

The antibodies of the present invention are useful in prevention and treatment of infections and diseases caused by *V. cholerae*, in particular *V. cholerae* O139.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 1 mg/kg to about 10 mg/kg body weight of the mammal, although a lower or higher dose may be administered.

The antibodies of the present invention are intended to be provided to the recipient subject in an amount sufficient to prevent, lessen or attenuate the severity, extent or duration of the infection by *V. cholerae*, in particular *V. cholerae* O139. Antibodies which immunoreact with DT may also be provided to a recipient subject in an amount sufficient to prevent, lessen or attenuate the severity, extent or duration of an infection by *Corynebacterium diptheriae*.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided either prior to the anticipated exposure to *V. cholerae*, in particular *V. cholerae* O139, (so as to attenuate the anticipated severity, duration or extent of an infection and disease symptoms) or after the initiation of the infection.

For all therapeutic, prophylactic and diagnostic uses, the oligo- or poly-saccharide of the invention, alone or linked to a carrier, as well as antibodies and other necessary reagents and appropriate devices and accessories may be provided in kit form so as to be readily available and easily used.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLES

The examples describe two methods for the synthesis of a conjugate comprising the capsular polysaccharide of *V. cholerae* O139, with a homobifunctional linker unit used for covalent attachment to a mutant diphtheria toxin as a model carrier protein. These examples are also described in reference 47.

Materials and Methods

Materials. Chicken serum albumin Fraction V (CSA), rabbit CSA antiserum, 1-ethyl-3-(3-dimethylaminopropyl)carbodiimide (EDC), adipic acid dihydrazide (ADH), 1-cyano-4-dimethylaminopyridinium tetrafluoroborate (CDAP), and agarose were from Sigma Chemical Co., St Louis, Mo.; SEPHAROSE™ (cross-linked agarose) CL-4B and SEPHADEX™ (cross-linked dextran) G-25 from Pharmacia AB, Uppsala, Sweden; BSA standard solution, Coomassie blue protein assay reagent, triethylamine (TEA) from Pierce, Rockford, Ill., nickel nitrilotriacetic acid (NiNTA) chelating agarose from Qiagen Inc., Chatsworth, Calif.; acetonitrile from T. J. Baker, Inc., Philipsburg, N.J.; diphtheria toxin (DT) from List Biological Laboratories, Inc, Campbell, Calif., equine antidiphtheria toxin, Lederle Laboratories, Pearl River N.Y., Lot 152-5456 R a gift from CBER, FDA; rabbit (3-4 week) complement from Pel-Freez, Brown Deer, Wis.; dialysis membranes (molecular weight cut off 6-8,000) from Spectra-Por, Laguna Hills, Calif.; ultrafiltration membrane YM100 and CENTRIPREP™ (cellulose membrane) 30 from Amicon, Inc, Beverly, Mass.; Limulus amebocyte lysate pyrogen (U.S. License No. 709) from BioWhittaker, Inc., Walkersville, Md.; tryptic soy broth (TSB) from Difco Inc, Detroit, Mich. (TSB containing 1% agarose was denoted as TSA). Deionized or pyrogen-free water (PFW) and pyrogen-free saline (PFS) were used in all experiments.

Bacteria. *V. cholerae* O139 MDO-12C [8], a heavily capsulated and opaque variant selected from the isolate MDO-12 (Madurai, India), was used for preparation of CPS and murine hyperimmune serum. *V. cholerae* O139 SPH1168, a clinical isolate from a Thai patient (Suanphung Hospital, Thailand), was used as the target strain in the vibriocidal assay. Both isolates were stored in 20% glycerol at −70° C.

Purification of *V. cholerae* O139 CPS. *V. cholerae* O139 MDO-12C was propagated from a single colony on TSA to 4×100 ml and then to 4×1 L of TSB for 5 h at 37° C. with shaking at 200 rpm. The 4-L inoculum ($A_{560}$~3.0) was transferred to a 300-L fermenter containing 150 L of TSB, 0.1% dextrose and 0.05 M $MgSO_4$. Fermentation was conducted at 30% dissolved oxygen, 35° C. and pH 7.0 (maintained with $NH_4OH$). After 16 h, formalin was added to a final concentration of 2% and stirred slowly for 6 h at room temperature. The suspension was centrifuged and the supernatant concentrated to 1.2 L by ultrafiltration and stored at −20° C.

A 500-mL aliquot of the concentrated supernatant was mixed with 3 volumes of 95% ethanol and stored overnight at 4° C. The supernatant was decanted and the slurry spun down at 10,500×g, 10° C. for 30 min. The pellet (20 g wet weight) was washed with 80% ethanol, dissolved in 800 ml of 10% saturated sodium acetate, pH 7.5, and extracted with cold phenol 3 times [9]. The final water phase was dialyzed against $H_2O$ for 3 days at 4-8° C. and freeze-dried. The precipitate was dissolved in 150 ml of 0.1 M $CaCl_2$ and ultracentrifuged at 145,000×g, 10° C. for 5 h. The supernatant was recentrifuged as above, dialyzed against $H_2O$, freeze-dried (yield 1.6 g) and stored at −20° C.

This material (unfractionated CPS) was dissolved in PFW (100 mg/50 ml) and passed through an Amicon membrane YM100. The retentate was passed through a 2.5×90 cm column of SEPHAROSE™ (cross-linked agarose) CL-4B in PFS. The retentate was eluted from the column as one peak at Kd 0.4. Colitose-containing fractions were pooled, dialyzed against PFW and freeze-dried. This material was denoted as CPS and used to prepare conjugates with rDT. In earlier experiments the filtration through the Amicon membrane was omitted (see preparation of CPS-AH conjugates below).

$^{13}C$ NMR spectroscopy. $^{13}C$ NMR spectrum of the CPS (50 mg/ml $D_2O$) was measured using Varian XL3000 spectrometer by averaging 50,000 scans with a 10-s decay between acquisition and 10-μs 90° pulse. Prior to Fourier transformation, a 5-Hz line broadening was applied and zero-filled to 32,000 datum points.

Murine hyperimmune *V. cholerae* O139 serum. *V. cholerae* O139 culture was prepared by transferring a single colony from TSA to 50 ml of LB and incubating at 37° C., 200 rpm for 5 h ($A_{560}$~1.0). The culture was inactivated with 1% formalin. Thirty 6-week-old female Swiss mice (NIH) were injected as follows: 1) 3 subcutaneous injections of 100 µL 1 day apart; 2) after 9 days, 3 intraperitoneal injections of 150 µL 1 day apart; 3) 9 days later, 3 intravenous injections of 200 µL 1 day apart. Mice were exsanguinated seven days after the last injection. All sera showed a precipitin line by double immunodiffusion with CPS: a pool was denoted as murine hyperimmune *V. cholerae* O139 serum.

Purification of recombinant diphtheria toxin mutant CRMH21G (rDT). The rDT was constructed by site-directed mutagenesis on the A chain replacing histidine at position 21 with glycine and expressed in *Escherichia coli* BL21 (λDE3) [15]. To facilitate purification by NiNTA, a 6-histidine tag was attached to the protein carboxyl terminal. Fermentation of this recombinant strain was performed as described [5]. The cell paste was suspended in 0.5 M NaCl, 0.02 M Tris, 0.005 M imidazole, pH 8.0 and the cytoplasm was released by a French press. The supernatant was passed through a 2.5×10 cm column NiNTA and washed with 0.02 M Tris buffer containing 0.03 M imidazole (pH 8.0). rDT was eluted with 0.02 M Tris buffer containing 0.25 M imidazole, pH 8.0 at 3-8° C. The eluate was dialyzed exhaustively against 0.02 M Tris, pH 8.0 at 3-8° C. (yield 150 mg rDT/L supernatant). Prior to derivatization, rDT was dialyzed at 3-8° C. against PBS with multiple changes of outer fluid followed by dialysis against 0.2 M NaCl, pH 7.2-7.7 (adjusted with 1 M NaOH). The protein solution was concentrated to ~10 mg/ml in an Amicon CENTRIPREP™ (cellulose membrane) 30.

rDT had the same $R_f$ in 10% SDS-PAGE and the same circular dichroism spectrum as DT. A line of identity was formed between rDT and DT when reacted against equine anti-DT by double immunodiffusion.

Adipic acid hydrazide (AH) derivatives. CPS was treated with ADH in the presence of CDAP [20, 21, 23], while CSA and rDT were treated with ADH in the presence of EDC [22, 37] as the activating agent.

AH derivative of CSA ($CSA_{AH}$). The AH derivative of CSA ($CSA_{AH}$) was prepared by EDC-mediated condensation of ADH and CSA [18]. Concentrations of the reactants in the reaction mixture were 10 mg CSA/mL, 0.2 M ADH, and 0.015 M EDC. ADH (powder) was added to the CSA, the pH adjusted to 5.5 with 0.1 M MES buffer (pH 5.5), and EDC (powder) was added. The reaction was carried out at room temperature, pH 5.5 to 5.7 for 1 h. The mixture was dialyzed overnight at 4° C. against saline and passed through a 2.5×40 cm column of SEPHADEX™ (cross-linked dextran) G-25 in saline. The void volume fractions were pooled, concentrated by ultrafiltration, stored at 4° C., and designated as $CSA_{AH}$.

AH derivatives of CPS $CPS_{AH}$. CDAP activation of CPS was performed as described [21] using a CDAP:CPS ratio of 1:5 (w/w). 40 mg of CPS (not filtered through an the Amicon YM100 membrane) was dissolved in 1.5 ml of $H_2O$; pH 5.0. 80 μL of CDAP in acetonitrile (100 mg/ml) were added with stirring followed in 30 sec with 80 μL of 0.2 M TEA. After 2 min, the pH was adjusted to 7.8 with 0.1 MHCl. Then 1.5 ml of 0.8 M ADH in 0.5 M $NaHCO_3$ was added and the pH maintained between 8.0 and 8.4 with 0.1 M HCl for 2 h at room temperature. The reaction mixture was dialyzed overnight against 6 L of water with 2 changes, and passed through a 2.5×40 cm column of SEPHADEX™ (cross-linked dextran) G-25 in PFW. The void volume fractions were freeze-dried, denoted as $CPS_{AH}$, and assayed for AH.

$CPS_{AH1}$. CPS which had been filtered through the Amicon YM100 membrane was employed. Concentrations of the reactants in the reaction mixture were 20 mg/mL of CPS, 0.05M ADH, and 0.05 M EDC. MES buffer (pH 5.5) was added to the CPS in water to adjust the pH to 5.5. EDC and ADH (both in powder form) were then added. The reaction was carried out for 2 h at room temperature and pH 5.5-5.6 was maintained with 0.5 M MES-acid. The pH was then brought to 7.0 with 0.1 M sodium phosphate buffer (pH 8.0), dialyzed overnight against water, and passed through a 1.5×24 cm column of Bio-gel P-10 in water. The void volume fractions were freeze-dried and designated as $CPS_{AH1}$.

$CPS_{AH2}$. CPS which had been filtered through the Amicon YM100 membrane was employed. The reaction was performed as described [21], at a CDAP/CPS ratio of 3:10 (w/w). 1 mL of CPS (30 mg/mL water), pH 5.0, was mixed with 90 μL of CDAP in acetonitrile (100 mg/mL). After 30 sec, 90 μL of 0.2 M TEA was added. During the next 2 min the pH dropped from 8.1 to 7.2, and 1 mL of 0.8 M ADH in 0.5 M NaHCO3 was added. The reaction was carried out for 2 h at room temperature and a pH 8.3-8.6 maintained with 0.1 M NaOH. The mixture was dialyzed overnight against water and passed through a 2.5×40 cm column of SEPHADEX™ (cross-linked dextran) G-25 in water. The void volume fractions were freeze-dried and denoted as $CPS_{AH2}$.

AH derivative of rDT ($rDT_{AH}$). The reaction mixture contained 10 mg/ml of protein, 0.2 M ADH and 0.011 M EDC. The reaction was carried out for 1 h at room temperature with the pH maintained at 6.2-6.4 with 0.1 M HCl. The reaction mixture was dialyzed against 0.2 M NaCl, pH 7.0 (adjusted with 1 M NaOH), and passed through a 1.5×25 cm column of SEPHADEX™ (cross-linked dextran) G-25 in the same solution. Void volume fractions were pooled, concentrated (Amicon CENTRIPREP™ (cellulose membrane) 30), denoted as $rDT_{AH}$, and assayed for protein and AH.

Conjugates with CSA. Two sets of conjugates, CPS-$CSA_{AH}$ and $CPS_{AH}$-CSA were prepared using EDC and CDAP as the activating agents [21, 22].

EDC-mediated synthesis of CPS-$CSA_{AH}$. The concentration of reactants in the reaction mixture were 10 mg/mL of CPS and 10 mg/mL of $CSA_{AH}$, and 0.02 M EDC. CPS was mixed with $CSA_{AH}$, and the pH was adjusted to 5.5 with 0.5 M MES buffer (pH 5.5). The mixture was brought to the final volume with saline, and EDC was added as powder. The reaction was carried out at room temperature for 3 h, during which the pH rose from 5.5 to 5.7. The conjugation was accompanied by a formation of precipitate that became gradually heavier. The mixture was dialyzed overnight against saline and centrifuged (7,000×g, 5 min) before passing through a 1.5×90 cm column of SEPHAROSE™ (cross-linked agarose) CL-2B in saline. Fractions were assayed for polysaccharide and protein. The fractions 21-29 of Vo peak were pooled and denoted as EDC:CPS-$CSA_{AH}$.

CDAP-mediated synthesis of CPS-$CSA_{AH}$. CPS was activated with CDAP and bound to $CSA_{AH}$ at a CDAP/CPS ratio of 3:10 (w/w). 10 mg of CPS in water (100 mg/mL) was mixed with 30 μL of CDAP in acetonitrile (100 mg/mL). The mixture (pH 5.2) was stirred for 30 sec, and 30 μL of 0.2 M TEA was added. After 2 min, 0.1 M NaOH was added to bring the pH from 7.0 to 8.2. $CSA_{AH}$ (10 mg) was added, and the volume adjusted with saline to 2 mL. The reaction was carried out for 3 h at room temperature, and a pH of 8.0 to 8.3 was maintained with 0.1 M NaOH. The mixture was passed through a 1.5×90 cm column of SEPHAROSE™ (cross-linked agarose) CL-2B in saline. Fractions were assayed for polysaccharide and protein. Fractions 30 to 46 were pooled and denoted as CDAP:CPS-$CSA_{AH}$.

EDC-mediated synthesis of $CPS_{AH1}$-CSA and $CPS_{AH2}$-CSA.

$CPS_{AH1}$-CSA. Concentrations of the reactants in the reaction mixture were 10 mg/mL of $CPS_{AH}1$, 10 mg/mL of CSA, and 0.02 M EDC. $CPS_{AH1}$ was mixed with CSA, and the pH was adjusted to 5.5 with 0.5 M MES buffer (pH 5.5). EDC was added as powder, and the mixture was brought to the final volume with saline. The reaction was carried out at room temperature for 3 h during which the pH rose from 5.5 to 5.6. The reaction mixture was passed through a 1.5×90 cm column of SEPHAROSE™ (cross-linked agarose) CL-2B in saline. Fractions were assayed for polysaccharide and protein. Fractions 36 to 52 were pooled and denoted as EDC:$CPS_{AH1}$-CSA.

$CPS_{AH2}$-CSA. Concentrations of the reactants in the reaction mixture were 5 mg/mL of $CPS_{AH2}$, 5 mg/mL of CSA, and 0.05 M EDC. The procedure was performed as described above. Fractions were assayed for polysaccharide and protein. Fractions 36 to 52 were pooled and denoted as EDC:$CPS_{AH2}$-CSA.

Conjugates with rDT. Two schemes were used to prepare conjugates with rDT: 1) EDC-mediated conjugation of the $CPS_{AH}$ with rDT, and 2) CDAP-mediated conjugation of the CPS with $rDT_{AH}$.

EDC-mediated conjugation of $CPS_{AH}$ with rDT. Each reaction mixture contained 8 mg/ml of $CPS_{AH}$ and of rDT, and EDC of 0.05 M (for I:$CPS_{AH}$-rDT) or 0.02 M (for II:$CPS_{AH}$-rDT).

$CPS_{AH}$ was dissolved in 0.2 M NaCl and the pH adjusted to 6.2 with 0.1 M NaOH. rDT was added and the volume adjusted with 0.2 M NaCl. After stirring for 1 min, EDC was added. The reaction was carried out for 3 h at room temperature and the pH maintained at 6.2-6.4 with 0.1 M HCl. The mixture was dialyzed overnight at 3-8° C. against 0.2 M NaCl, 0.005 M sodium phosphate, pH 7.5, and passed through a 1.5×90 cm column of SEPHAROSE™ (cross-linked agarose) CL-4B in the same buffer. Fractions were assayed for polysaccharide and protein. The void volume fractions were pooled and denoted as I:$CPS_{AH}$-rDT and II:$CPS_{AH}$-rDT.

CDAP-mediated conjugation of CPS with $rDT_{AH}$. Each reaction mixture contained 8 mg/ml of CPS and of $rDT_{AH}$: the CDAP/CPS was 4:5 (for I:CPS-$rDT_{AH}$) or 1:5 (for II:CPS-$rDT_{AH}$).

CDAP (100 mg/ml acetonitrile) was added to CPS in 0.2 M NaCl (pH 5.2) and mixed for 30 sec. An equal volume of 0.2 M TEA to that of CDAP was added. After 2 min, the pH dropped from 8.5 to 7.2 and $rDT_{AH}$ was added. The pH was raised from 7.2 to 8.3 with 0.1 M NaOH. The reaction was carried out for 2 h at room temperature during which the pH was stable. The mixture was dialyzed overnight against 0.2 M NaCl, 0.005 M sodium phosphate buffer, pH 7.5, and passed through a 1.5×90 cm column of SEPHAROSE™ (cross-linked agarose) CL-4B in the same buffer. Fractions were assayed for polysaccharide and protein and void volume fractions pooled and denoted as I:CPS-$rDT_{AH}$ and II:CPS-$rDT_{AH}$.

Chemical assays. Polysaccharide was assayed by measuring 3,6-dideoxyhexose (colitose) with the CPS as the standard [18]. Protein was measured by Coomassie blue assay with BSA as the standard [2]. Hydrazide content of $CPS_{AH}$ and $rDT_{AH}$ was measured by the TNBS method using ADH as the standard [14]. The degree of derivatization was expressed in % of AH, and the mol/mol ratio of AH to polysaccharide or to protein.

Limulus amebocyte lysate test. CPS was assayed for endotoxin by limulus amebocyte lysate test. The FDA Reference Standard Endotoxin (Lot EC-5) was used as a reference for the assay. The test conforms with the FDA guideline [41].

Immunodiffusion. Double immunodiffusion of the conjugates was performed in 1% agarose gel in 0.15 M NaCl with murine hyperimmune cholera O139 serum and equine diphtheria toxin antiserum.

Immunization of mice. Six-week-old female Swiss albino mice (10 per group) were injected subcutaneously 3 times at 2-week intervals with 100 µL of immunogen containing 2.5 µg of the CPS alone or as the conjugate. A control group received 1 injection of 100 µL of saline. Mice were exsanguinated 7 days after each injection and sera stored at –20° C.

ELISA. Flat-bottom 96-well microtiter plates (NUNC-IMMUNO™ (coated polystyrene), Denmark) were coated with CPS (20 µg/ml PBS) and kept overnight at room temperature. After washing with 0.15 M NaCl, 0.1% Brij and 3 mM sodium azide, plates were blocked with 1% BSA in PBS for 2 h at room temperature. The plates were washed and 2-fold serial dilutions of sera in 1% BSA, 0.1% Brij, PBS added. Reference serum was assayed in triplicates and samples in duplicates. Plates were incubated overnight at room temperature, washed, and the alkaline phosphatase-labeled goat antibody specific to mouse IgG or for IgM was added. After 4 h at room temperature, the plates were washed, and the 4-nitrophenyl phosphate substrate (1 mg/ml in 1 M Tris-HCl, 3 mM $MgCl_2$, pH 9.8) was added. $A_{405}$ was measured by a MRX Dynatech reader.

Anti-CPS IgG was measured in all murine sera; anti-CPS IgM was measured only in 11 representative sera from mice injected 3 times with II:$CPS_{AH}$-rDT or I:CPS-$rDT_{AH}$. Murine hyperimmune *V. cholerae* O139 serum was used as the reference for both anti-CPS IgG and IgM. This serum was arbitrarily assigned a value of 1000 ELISA units/ml (EU) for IgG and 100 EU for IgM upon the observation that 1/20,000 dilution of anti-IgG and 1/100 dilution of anti-IgM gave approximately the same $A_{405}$.

An analogous ELISA procedure was used to measure anti-DT IgG: plates were coated with DT (5 µg/ml) and a mouse serum with high titer of anti-DT IgG, arbitrarily assigned a value of 1000 EU, served as the reference.

ELISA results were computed with an ELISA Data Processing Program provided by the Biostatistics and Information Management Branch, CDC based upon four parameters logistic-log function using Taylor Series Linearization Algorithm [34]. Anti-CPS IgG and anti-DT IgG levels are expressed as geometric means.

Statistics. Comparisons of the geometric means were performed with the two-sided t test or Wilcoxon analysis.

Vibriocidal assay. Eleven representative sera from mice injected three times with II:$CPS_{AH}$-rDT or I:CPS-$rDT_{AH}$, and twenty convalescent sera from cholera patients infected with *V. cholerae* O139 (Samutskakorn Hospital, Thailand) [13] were assayed for vibriocidal activity before and following treatment with 0.1 M 2-ME for 30 min at 37° C. [10, 27]. The patient sera were also tested for fibriocidal activity after absorption with CPS in vibriocidal antibody inhibition assay (VAI) [6].

Bacteria were prepared by transferring a single colony from TSA into 10 ml of TSB and incubating for 2 to 3 h at 37° C. with shaking at 180 rpm. 100 µL of this inoculum was transferred to 10 ml of TSB and incubated with shaking (180 rpm) at 37° C. until culture reached $A_{560}$ of 0.2-0.24 (3.0-4.0× $10^7$ cells/ml). The bacterial suspension was diluted $10^5$-fold in Dulbecco's buffer.

Vibriocidal assay was performed in sterile non-pyrogenic 24-well cell culture plates (Costar, Corning, N.Y.) by mixing equal volumes of serum, bacteria and complement. The tested serum was 2-fold serially diluted in Dulbecco's buffer (for VAI in 100 mg CPS/ml Dulbecco's buffer), so that each well contained 100 μL. 100 μL aliquots of the bacteria and of complement were added into each well. Plates were incubated for 1 h at 37° C. with shaking. Two 100 μL aliquots from each well were transferred into empty wells and 1 ml of TSA (46-48° C.) added to all 3 wells. Plates were incubated overnight at 37° C. and the colonies counted. The vibriocidal titer was defined as the reciprocal of the highest serum dilution showing ≧60% reduction in number of colonies compared to the control (complement only) [25].

Results

Figure 2:
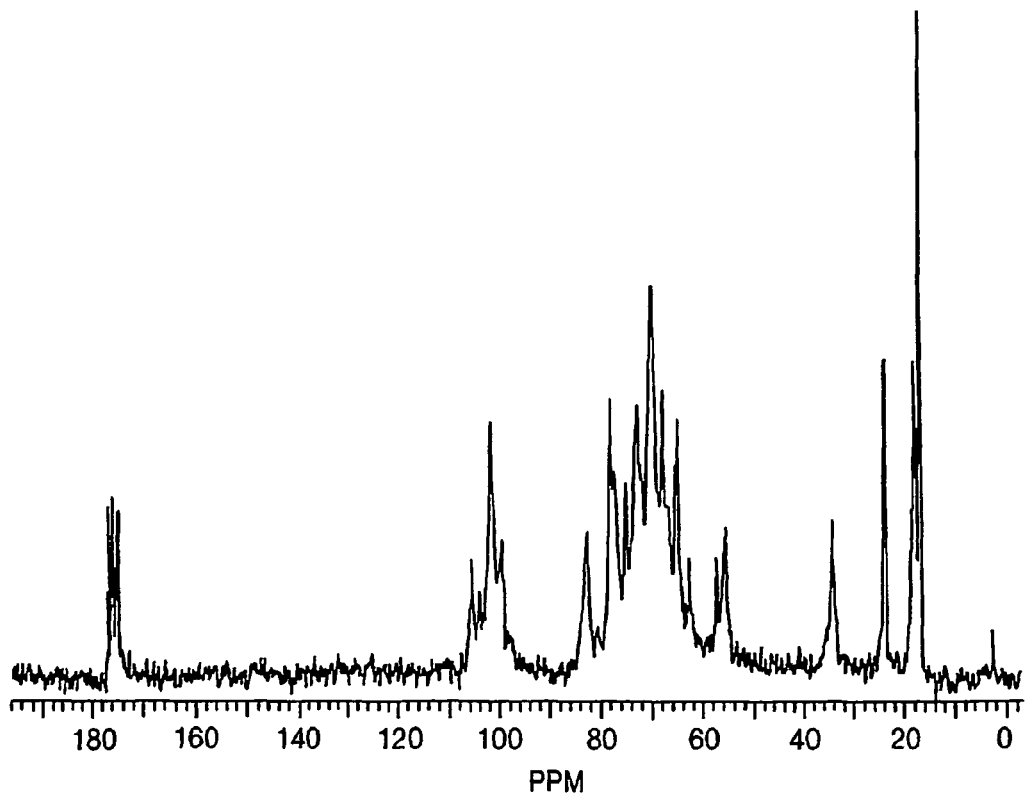

*V. cholerae* O139 CPS. The *V. cholerae* O139 CPS isolated from culture supernatant (Material and Methods) showed three peaks at Kds of 0.4, 0.71 and 0.91 on SEPHAROSE™ (cross-linked agarose) CL-4B with yields of 70%, 29% and 1%, respectively (FIG. 1). Colitose, a component of the CPS-repeating unit, was detected only in the peak at Kd 0.4. Fast separation of this peak-material from the lower molecular weight materials (Kds 0.71 and 0.91) was accomplished by diafiltration of the unfractionated CPS through an Amicon membrane YM100. To confirm its purity, the retentate was passed through SEPHAROSE™ (cross-linked agarose) CL-4B and showed only a peak of Kd 0.4. $^{13}$C-NMR spectrum of the retentate (equivalent to the peak-material of Kd 0.4) [FIG. 2] was identical to a published $^{13}$C NMR spectrum of *V. cholerae* O139 CPS [19, 35]. The filtrate spectrum, in contrast, lacked chemical shifts for colitose, quinovosamine, GluNAc and D-galacturonic acid. The retentate gave strong reaction with the murine *V. cholerae* O139 hyperimmune serum by Western blot and double immunodiffusion. The retentate, denoted as the CPS, showed only <0.5 endotoxin units/μg as measured by limulus amebocyte lysate test. Fractions not containing colitose were not antigenic.

AH derivatives of CSA. $CSA_{AH}$ contained ~9 moles of AH per mole CSA. $CSA_{AH}$ formed a line of identity with CSA when reacted with rabbit anti-CSA serum by double-immunodiffusion.

AH derivatives of CPS ($CPS_{AH}$, $CPS_{AH1}$, $CPS_{AH2}$,) and rDT ($rDT_{AH}$) [Table 1]. $CPS_{AH1}$, prepared by EDC-mediated reaction, contained 0.08 moles of hydrazide per mole of CPS-repeating unit. $CPS_{AH2}$, prepared by the CDAP method, contained 0.12 moles of hydrazide per mole of CPS repeating unit. $CPS_{AH}$ contained 3.4% of AH, which represents ~1 AH per 5 CPS-repeating units. All three AH derivatives formed a line of identity with CPS when reacted with murine hyperimmune *V. cholerae* O139 serum by double immunodiffusion.

$rDT_{AH}$ contained 7.2 moles of AH per mole of protein and formed a line of identity with rDT when reacted with equine DT antiserum by double immunodiffusion.

TABLE 1

Adipic acid hydrazide derivatives (AH) of *Vibrio cholerae* O139 capsular polysaccharide (CPS) and of recombinant diphtheria toxin mutant (rDT)

| Derivative | Activating agent | AH content % | mol/mol* |
|---|---|---|---|
| $CPS_{AH}$ | CDAP | 3.44 | 0.21 |
| $rDT_{AH}$ | EDC | 1.90 | 7.12 |

*CPS-repeating unit ($M_r$ 1053), rDT ($M_r$ ~ 67,000)

Figure 3A:
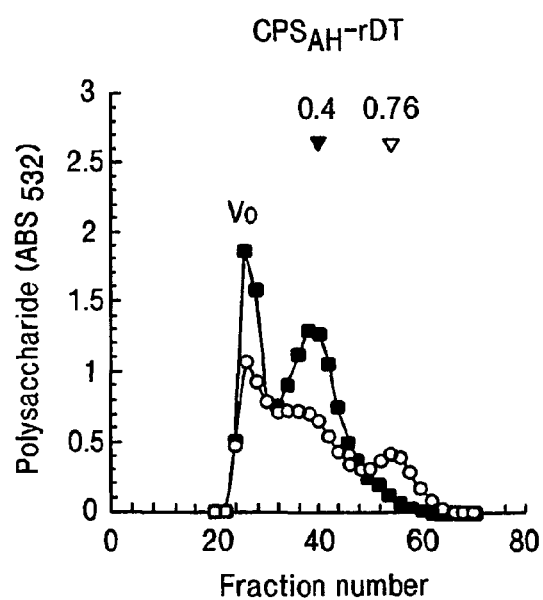
Figure 3B:
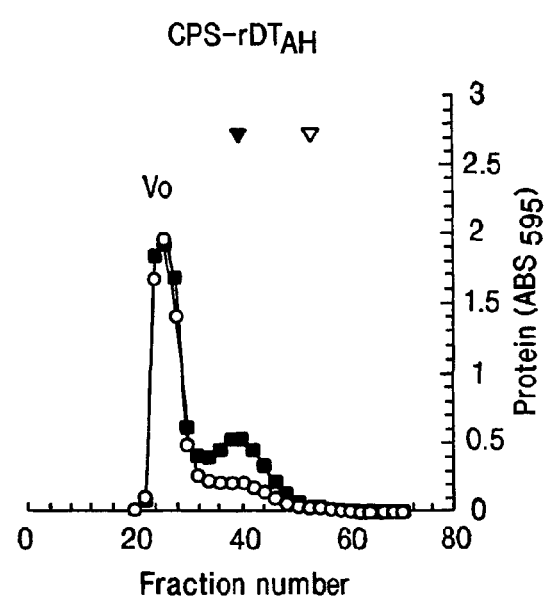
Figure 4A:
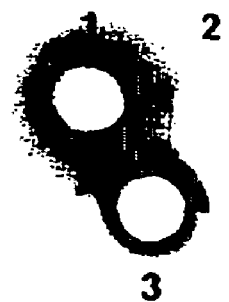
Figure 4B:
Figure 5:
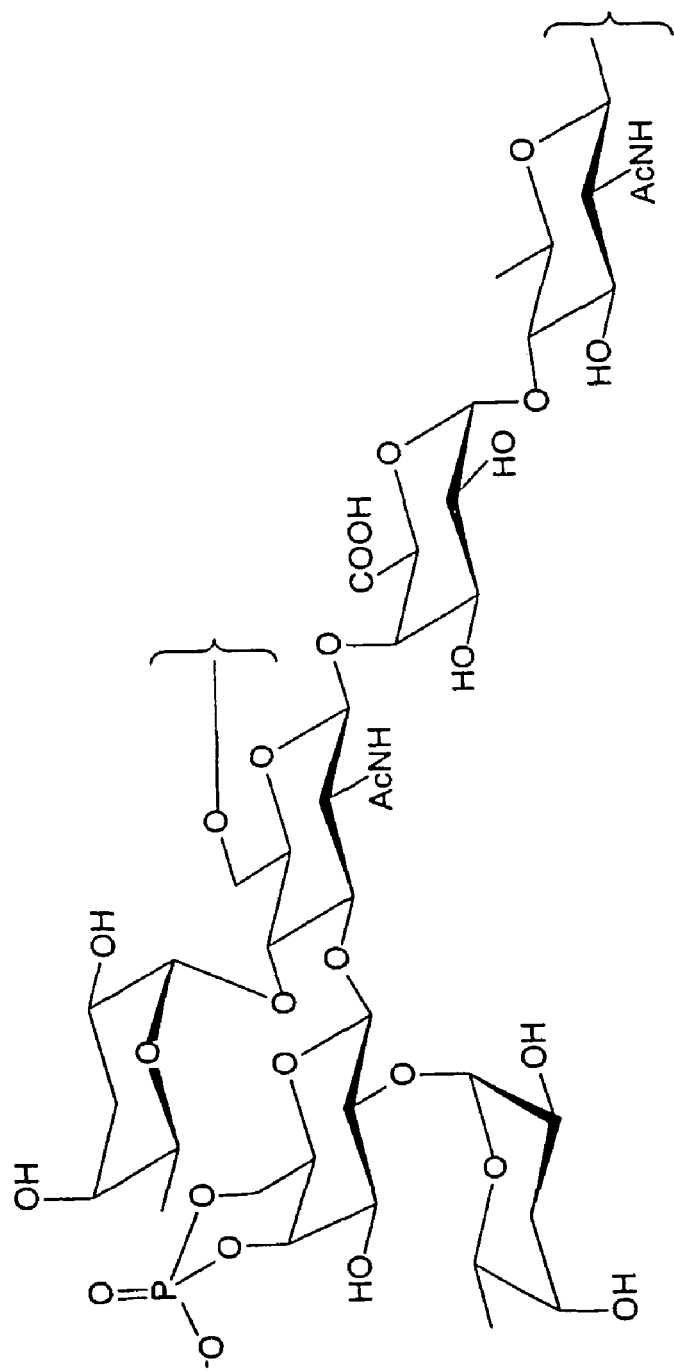

Conjugates. (FIG. 3, Table 2).

EDC-mediated synthesis of $CPS_{AH}$-CSA conjugates (EDC:CPS-$CSA_{AH}$). Gel filtration profile of this conjugate, prepared by EDC-mediated binding of CPS to $CSA_{AH}$, showed 2 peaks (Vo and Kd 0.52) that contained both polysaccharide (PS) and proptein (PR). The Vo material consisted mostly of PR (PS/PR 0.15). The majority of PS was detected in the second peak (Kd 0.52). Formation of this conjugate was accompanied by the development of a protein precipitate that accounted for about 30% of total PR. Only Vo material was included in the final pool of the conjugate, and the yield (by the recovery of PS) was 2.7%.

CDAP-mediated synthesis of $CPS_{AH}$-CSA conjugates (CDAP:CPS-$CSA_{AH}$). This conjugate was prepared from the same components as EDC:CPS-$CSA_{AH}$ but using CDAP as the activating agent. Gel filtration of this conjugate showed that PS was present in fractions 30-65, similar to the elution range of CPS alone (34-60). PR was detected within Fr 30-70, that is 20 fractions before the elution range of CSA alone. Only fractions 30-47 of the PS and PR overlapping region were included in the final pool of the conjugate. The PS/PR ratio of the conjugate was 2.6, and the yield based on the recovery of PS was 51%.

EDC-mediated synthesis of $CPS_{AH}$-CSA conjugates (EDC:$CPS_{AH1}$-CSA and EDC:$CPS_{AH2}$-CSA). Both conjugates were prepared by EDC-mediated conjugation of the AH derivative of CPS with CSA, but the w/w ratio of EDC/PR was 5-fold higher in the synthesis of EDC:$CPS_{AH2}$-CSA. It should be also noted that $CPS_{AH1}$ and $CPS_{AH2}$ had a different content of hydrazide and were prepared by different derivatization reactions. Gel filtration of the conjugates showed that PS and PR peaks overlapped in the range of 36-52 (EDC:$CPS_{AH1}$-CSA) and 36-60 (EDC:$CPS_{AH2}$-CSA). There was more PR eluted at Kd 0.78 (identical to Kd of CSA alone) in the first conjugate. Only fractions 36-52 were included in the final pools of each conjugate. The PS/PR (w/w) ratio and yield, by the recovery of PS, were higher for EDC:$CPS_{AH1}$-CSA than for EDC:$CPS_{AH2}$-CSA.

EDC-mediated synthesis of $CPS_{AH}$-rDT conjugates. Identical reaction conditions, except for the concentration of EDC, were used to prepare I:$CPS_{AH}$-rDT (0.05 M EDC) and II:$CPS_{AH}$-rDT (0.02 M EDC). gel filtration of either conjugate on SEPHAROSE™ (cross-linked agarose) CL-4B yielded 3 peaks at Vo, Kd 0.4 and Kd 0.76 (FIG. 3A). Two peaks, at Vo and Kd 0.4, consisted of both polysaccharide and protein, while the peak at Kd 0.76 contained only protein. Since the Kds of the free CPS and rDT on SEPHAROSE™ (cross-linked agarose) CL-4B are 0.4 and 0.76, respectively, the presence of unreacted CPS and/or rDT within the range of Kd 0.4-0.76 could not be excluded. Accordingly, only the void volume fractions were pooled and denoted as I:$CPS_{AH}$-rDT and II:$CPS_{AH}$-rDT.

I:$CPS_{AH}$-rDT had a lower polysaccharide/protein ratio (w/w) than II:$CPS_{AH}$-rDT (0.46<0.76). The yields of both conjugates were about 20% based upon the recovery of polysaccharide. Double immunodiffusion of either conjugate against murine *V. cholerae* O139 and equine DT toxin hyperimmune sera showed a single precipitin line (FIG. 4A).

CDAP-mediated synthesis of CPS-$rDT_{AH}$ conjugates. I:CPS-$rDT_{AH}$ and II:CPS-$rDT_{AH}$ were prepared under the same conditions except for the w/w ratio of CDAP/CPS that was 4:5 and 1:5, respectively. Gel filtration of either conjugate on SEPHAROSE™ (cross-linked agarose) CL-4B showed 2 peaks (Vo and Kd 0.4) both containing polysaccharide and protein (FIG. 3B). The void volume fractions were pooled and denoted as conjugates I:CPS-$rDT_{AH}$ and II:CPS-$rDT_{AH}$: their polysaccharide/protein ratios were 0.99 and 0.90, respectively. The yield of I:CPSr$DT_{AH}$ was 45%. The yield of II:CPS-$rDT_{AH}$ could not be determined because of an accidental loss of some material. Both conjugates formed a single precipitin line when reacted with murine *V. cholerae* O139 and equine DT hyperimmune sera by double immunodiffusion (FIG. 4B).

The structural differences between CPS-rDT$_{AH}$ and CPS$_{AH}$-rDT are unknown, but differing points of attachment and differing levels of crosslinking seem likely.

TABLE 2

Composition of *V. cholerae* O139 capsular polysaccharide (CPS) conjugates with recombinant diphtheria toxin mutant (rDT).

| Conjugate | Conjugation Method | PS/PR (w/w) | Yield* |
|---|---|---|---|
| I:CPS$_{AH}$-rDT | EDC (0.05 M) | 0.46 | 28.0% |
| II:CPS$_{AH}$-rDT | EDC (0.02 M) | 0.78 | 20.1% |
| I:CPS-rDT$_{AH}$ | CDAP:CPS (4:5) | 0.90 | 45.0% |
| II:CPS-rDT$_{AH}$ | CDAP:CPS (1:5) | 0.99 | ** |

*Yield determined by the amount of polysaccharide in conjugate
**Accidental loss of some material prevented accurate determination Serum antibody responses elicited by conjugates (Table 3).

Anti-CPS IgG: All conjugates elicited a significant rise after the second injection (P<0.006). Among the rDT conjugates, only II:CPS$_{AH}$-rDT, I:CPS-rDT$_{AH}$ and II:CPS-rDT$_{AH}$ elicited a booster after third injection (P<0.003).

Anti-DT IgG: All rDT conjugates elicited significant rises after the 2nd and 3rd injections. After the third injection, II:CPS$_{AH}$-rDT elicited the highest and statistically significantly different level compared to other conjugates (P<0.0007).

Anti-CPS IgG. CPS alone did not elicit an antibody response compared to saline (0.22 vs. 0.19, NS).

None of the rDT conjugates elicited a statistically significant antibody response after the first dose. All four conjugates elicited significant rises of anti-CPS IgG after the second dose (P<0.006). However, only II:CPS$_{AH}$-rDT, I:CPS-rDT$_{AH}$ and II:CPS-rDT$_{AH}$, elicited a booster response following the third dose compared to the second one (P<0.003). There were no significant differences between the post-third levels elicited by these three conjugates (10.3 vs. 11.5 vs. 4.21 NS): all were significantly higher than those elicited by I:CPS$_{AH}$-rDT (10.3, 11.5, 4.21 vs. 0.43, P<0.0001).

Anti-diphtheria toxin IgG. All conjugates elicited significant rises of anti-DT IgG after the second and third injections compared to the first injection (P<0.0001). II:CPS$_{AH}$-rDT induced the highest level of anti-DT IgG of all conjugates, however, only the post-third injection level was statistically significantly higher (1050 vs. 245, 255, 279, P<0.0007).

TABLE 3

Serum IgG response specific to CPS and DT elicited in mice (n = 10/group) by *V. cholerae* O139 CPS conjugates with rDT

| Conjugate | Dose | ELISA units/ml (25-75 centiles) anti-cps IgG | anti-DT IgG |
|---|---|---|---|
| I:CPS$_{AH}$-rDT | 1 | 0.13 (0.11-0.17) | 0.05 (0.03-0.06) |
| | 2 | 0.35 (0.24-0.5) | 52.8 (33.8-87.4) |
| | 3 | 0.43 (0.28-0.58) | 254. (121-376) |
| II:CPS$_{AH}$-rDT | 1 | 0.23 (0.16-0.28) | 0.60 (0.2-2.6) |
| | 2 | 1.04 (0.35-0.68) | 186. (155-233) |
| | 3 | 10.3 (1.67-12.2) | 1050. (715-1210) |
| I:CPS-rDT$_{AH}$ | 1 | 0.11 (0.11-0.14) | 0.70 (0.37-1.3) |
| | 2 | 0.89 (0.39-1.14) | 81.1 (52.3-128) |
| | 3 | 11.5 (4.99-29.7) | 255. (128-548) |
| II:CPS-rDT$_{AH}$ | 1 | 0.22 (0.18-0.27) | 0.80 (0.34-2.8) |
| | 2 | 0.49 (0.35-0.68) | 146. (90-214) |
| | 3 | 4.21 (1.67-12.2) | 279. (175-388) |

CPS alone after 3 injections did not elicit anti-CPS IgG as compared to saline (0.21 EU vs 0.19 EU, NS).

Vibriocidal activity of murine sera (Table 4). Representative sera from mice injected 3 times with CPS conjugates were tested for vibriocidal activity. The CPS-rDT conjugate induced titers ranged from 1600-6400: II:CPS$_{AH}$-rDT induced slightly higher titers (3200-6400) than I:CPS-rDT$_{AH}$ (1600-3200). These two groups of sera showed a similar range of anti-CPS IgG levels, while the anti-CPS IgM levels were slightly higher in mice injected with II:CPS$_{AH}$-rDT than with I:CPS-rDT$_{AH}$. Similar vibriocidal results were demonstrated with the heavily capsulated *V. cholerae* O139 MDO12C variant (the strain which was used for purification of the CPS) and other clinical isolates as the target strains.

Following treatment with 2-ME, the vibriocidal titers of most sera declined about 4-fold, however, all retained significant levels of vibriocidal activity.

TABLE 4

Vibriocidal activity of representative sera from mice injected 3 times with the conjugates of *V. cholerae* O139 capsular polysaccharide (CPS) and chicken serum albumin (CSA) or recombinant diphtheria toxin mutant (rDT).

| Conjugate | anti-CPS (EU) IgG | IgM | vibriacidal titer untreated serum | treated with 2-ME |
|---|---|---|---|---|
| CDAP:CPS-CSA$_{AH}$ | 18.4 | 1.68 | 1000 | — |
| | 73.9 | 1.67 | 2000 | — |
| | 102.3 | 1.50 | 1000 | — |
| | 325.0 | 11.53 | 8000 | — |
| EDC:CPS$_{AH1}$-CSA | 14.5 | 2.51 | 2000 | — |
| | 58.9 | 2.38 | 4000 | — |
| | 71.9 | 0.91 | 2000 | — |
| | 118.1 | 2.50 | 2000 | — |
| EDC:CPS$_{AH}$-CSA | 18.1 | 2.38 | 1000 | — |
| | 62.4 | 2.21 | 2000 | — |
| | 70.3 | 2.32 | 4000 | — |
| | 103.5 | 9.92 | 4000 | — |
| II:CPS$_{AH}$-rDT | 13.2 | 5.43 | 3200 | 400 |
| | 17.5 | 3.64 | 1600 | 400 |
| | 42.2 | 6.94 | 3200 | 800 |
| | 54.5 | 9.11 | 6400 | 1600 |
| | 180.8 | 10.5 | >6400 | 1600 |
| I:CPS$_{AH}$-rDT | 15.5 | 4.02 | 1600 | 400 |
| | 18.9 | 1.45 | 1600 | 800 |
| | 27.2 | 2.05 | 1600 | 200 |
| | 29.7 | 2.38 | 1600 | 400 |
| | 36.3 | 2.54 | 3200 | 800 |
| | 68.5 | 2.32 | 3200 | 800 |

Serum anti-CPS IgG and IgM levels are expressed in ELISA units/ml (EU) compared to a murine hyperimmune cholera O139 serum arbitiarily assigned 1000 EU for anti-CPS IgG and 100 EU for anti-CPS IgM. The vibriocidal assay was performed with *V. cholerae* O139 isolate SPH1168 as the target strain and 2-fold serially diluted sera starting from 1:50 dilution. The vibriocidal titer is defined as the reciprocal of the highest serum dilution that caused a ≧60% reduction in the number of bacteria compared to the complement control. Sera from mice injected with saline or CPS had vibriocidal titer <50.

Vibriocidal activity in convalescent sera of cholera patients infected with *V. cholerae* O139 (Table 5). Vibriocidal titers of 20 patient sera ranged from 100 to 6400. After absorption with CPS, titers of all sera declined to ≦50 (baseline for the assay).

Treatment with 2-ME reduced the vibriocidal activity to ≦50 in 17/20 sera. The vibriocidal titer of SK 639-2 remained at the same level (400) as found in the untreated serum.

TABLE 5

Serum vibriocidal titers of convalescent sera from patients infected with *V. cholerae* O139 measured before and after absorption with CPS or treatment with 2-mercaptoethanol (2-ME)

| Patient ID | untreated | vibriocidal titer CPS-absorbed | 2-ME-treated |
|---|---|---|---|
| SK 391-2 | 3200 | <50 | <50 |
| SK 395-2 | 1600 | <50 | <50 |
| SK 428-2 | 800 | <50 | <50 |
| SK 456-2 | 400 | <50 | <50 |
| SK 458-2 | 3200 | <50 | <50 |
| SK 494-2 | 100 | <50 | <50 |
| 5K 504-2 | 400 | <50 | <50 |
| SK 522-2 | 1600 | <50 | 50 |
| SK 577-2 | 1600 | <50 | <50 |
| SK 591-2 | 1600 | <50 | <50 |
| SK 597-2 | 800 | <50 | <50 |
| SK 599-2 | 3200 | <50 | <50 |
| SK 622-2 | 400 | <50 | 50 |
| 5K 639-2 | 400 | <50 | 400 |
| SK 646-2 | 3200 | <50 | <50 |
| 5K 720-2 | 1600 | <50 | <50 |
| SK 741-2 | 800 | <50 | <50 |
| SK 749-2 | >6400 | <50 | 100 |
| SK 755-2 | 1600 | <50 | 200 |
| SK 760-2 | 1600 | <50 | 50 |

Each vibriocidal assay was performed with 2-fold serially diluted tested serum starting from a 1:50-dilution and using *V. cholerae* O139 SPH1168 as the target strain.

Discussion

Probably because of its complex structure [19, 35] and relatively tight folded conformation [11], development of synthetic schemes for preparation of *V. cholerae* O139 CPS conjugate vaccine was difficult and required the use of a readily available protein carrier (chicken serum albumin, CSA) to optimize the synthetic methods. Slight modifications of the two most successful synthetic schemes were then used to prepare conjugates with the medically useful rDT.

Both synthetic schemes involved adipic acid dihydrazide as the linker and two different activating agents, CDAP and EDC. CDAP was used to prepare AH derivative of CPS (CP-S$_{AH}$), and EDC was used to prepare CSA$_{AH}$ and rDT$_{AH}$. Conjugation of CPS$_{AH}$ with rDT and CSA was mediated by EDC; alternatively conjugates were prepared by binding rDT$_{AH}$ and CSA$_{AH}$ with CDAP-activated CPS.

Conjugates such as EDC:CPS-CSA$_{AH}$ and CDAP:CPS-CSA$_{AH}$, although prepared from the same components but using different activating agents, are structurally different molecules. EDC activates carboxyls, while CDAP activates hydroxyls for the reaction with nucleophilic groups [63, 64]. In addition, the chemistry of both conjugations is complex because the potentially activated groups (carboxyls or hydroxyls) are present on both CPS as well as CSA$_{AH}$, and they can react with both hydrazides and amines (ε amine group of lysine) on the protein. It should be pointed out that hydrazides are stronger nucleophiles than amines, therefore, activated carboxyls or hydroxyls will react preferentially with hydrazides.

Synthesis of EDC:CPS-CSA$_{AH}$ is representative of several conjugation experiments: all were accompanied with precipitation of protein, and the resultant conjugates were large in molecular size, had low w/w PS/PR ratios ($\leq 0.15$), and were poor immunogens. Together these findings indicate that during EDC-mediated conjugation of CPS and CSA$_{AH}$ the protein became self-cross-linked, and such structural alteration of carrier protein could explain the low immunogenicity of this conjugate. Self-cross-linking of protein could be a direct result of the comparatively higher reactivity of the CSA-carboxyls than the CPS-carboxyls.

In contrast, no protein precipitation was observed during EDC-mediated binding of CPS$_{AH}$ with CSA. In this synthesis the higher reactivity of protein carboxyls relative to CPS carboxyls favors the reaction of protein carboxyls with they hydrazides of CPS$_{AH}$, which results in the formation of conjugate. The lower reactivity of CPS carboxyls reduces the extent of self-crosslinking of CPS molecules. Both resultant conjugates, EDC:CPS$_{AH1}$-CSA and EDC:CPS$_{AH2}$-CSA, had high PS/PR ratios and were significantly better immunogens than EDC:CPS-CSA$_{AH}$.

In contrast to the EDC-mediated coupling of CPS to CSA$_{AH}$, the CDAP-mediated coupling of the same components resulted in the formation of the highly immunogenic conjugate CDAP:CPS-CSA$_{AH}$. It is also of interest, that although CSA$_{AH}$ was prepared by an EDC-mediated derivatization, this exposure to relatively mild conditions (10 mM EDC for 1 h) had no apparent negative effect on the carrier protein or on the immunogenicity of the resultant conjugate.

The resultant conjugates elicited serum anti-CPS IgG after the second injection and a booster after the third injection when administered to mice by a clinically relevant method and route. Similarly to the immunologic properties of the *V. cholerae* O1 serotype Inaba O-specific polysaccharide conjugates with cholera toxin [10], the *V. cholerae* O139 CPS-CSA and CPS-rDT conjugates elicited high titers of serum vibriocidal antibodies in mice. Treatment with 2-ME reduced (~4-fold) but did not eliminate the CPS-rDT induced vibriocidal activity, indicating that much of this activity was mediated by anti-CPS IgG.

I:CPS-rDT$_{AH}$ elicited the highest level of anti-CPS IgG after the third injection (11.4 EU) but this was not statistically different from the levels elicited by II:CPS$_{AH}$-rDT (10.3 EU) or II:CPS-rDT$_{AH}$ (4.21 EU). On the basis of these data, we plan to clinically evaluate I:CPS-rDT$_{AH}$ and II:CPS$_{AH}$-rDT.

All four conjugates elicited significant rises of anti-DT IgG after the second and third injections. II:CPS$_{AH}$-rDT elicited the highest post-third injection level of anti-DT IgG that was significantly different from those of other 3 conjugates (P<0.0007).

I:CPS$_{AH}$-rDT, prepared by synthesis of CPS$_{AH}$ with rDT at the higher concentration of EDC (0.05 M), elicited the lowest level of anti-CPS IgG. The level of anti-DT IgG induced by this conjugate was comparable to those elicited by both of CPS-rDT$_{AH}$ indicating that there was no correlation between the antibody elicited to the CPS and to the protein carrier.

There is some confusion about the vibriocidal activity of convalescent sera from patients infected with *V. cholerae* O139 [3, 17, 25, 28, 40]. We found that patient sera convalescent from cholera O139 were uniformly vibriocidal. The data variation among laboratories may be explained by the different complement dilutions used for the vibriocidal assays. We found that highly diluted complement, used in the vibriocidal assay for *V. cholerae* O1, is not sufficient to mediate killing of *V. cholerae* O139 which has a capsule. We showed that the undiluted baby rabbit serum, as the source of complement, is a reliable reagent to demonstrate antibody-initiated lysis of *V. cholerae* O139.

Similar to the serologic response of humans to the *V. cholerae* O1 infection [1, 24, 29, 32, 34], our results showed that vibriocidal activity of sera from patients infected with serotype O139 was mostly specific to its surface polysaccharide (CPS) and mediated by IgM. This is also true for parenterally administered killed whole cell cholera O1 vaccine or orally administered attenuated cholera O1 strains [7, 27, 44]. In contrast, parenterally administered polysaccharide-protein conjugate vaccines elicit, in addition to IgM, high levels of serum anti-polysaccharide IgG (2-ME resistant) [10, 38]. We proposed that it is IgG that penetrates on to the intestinal epithelium and initiates complement-mediated lysis of the bacterial inoculum and that measurement of the conjugate-induced serum IgG specific to the surface polysaccharides of both *V. cholerae* O1 and O139 should provide a reliable method for standardization of these vaccine candidates [36, 39].

Diafiltration through YM100 allowed a rapid separation of the low molecular weight impurities from *V. cholerae* O139 CPS. When the material eluted at Kd 0.91 from SEPHAROSE™ (cross-linked agarose) CL-4B, representing only 1% (by weight) of the unfractionated CPS, was concentrated 100-fold and analyzed by SDS-PAGE/Western blot with murine hyperimmune cholera O139 antiserum, it showed two fast-moving bands, similar to that reported for LPS of *V. cholerae* O139 [4, 45]. Our results indicate that diafiltration could be adapted for rapid separation of CPS and/or LPS from other medically useful polysaccharides.

In summary, *V. cholerae* O139 CPS conjugates with rDT elicited high levels of serum anti-CPS IgG in mice with vibriocidal activity. The vibriocidal activity of convalescent sera from patients infected with *V. cholerae* O139 was mediated mostly by anti-CPS IgM. To verify whether a critical level of anti-CPS IgG will confer immunity to *V. cholerae* O139, clinical trials of the two most immunogenic CPS-rDT conjugates are planned.

REFERENCES

1. Benenson, A. S., A. Saad, and W. H. Mosley. 1968. Serological studies in cholera. 2. The vibriocidal antibody response of cholera patients determined by a microtechnique. *Bull. W.H.O.* 38:277-285.

2. Bradford, M. M. 1976. A rapid and sensitive method for the quantitation of microgram quantities of protein utilizing the principle of protein-dye binding. *Anal. Biochem.* 72:248-254.

3. Coster, T. S., K. P. Killeen, M. K. Waldor, D. T. Beattie, D. R. Spriggs, J. R. Kenna, A. Trofa, J. C. Sadoff, J. J. Mekalanos, and D. N. Taylor. 1995. Safety, immunogenicity, and efficacy of live attentuated *Vibrio cholerae* O139 vaccine prototype. *Lancet* 345:949-952.

4. Cox, A. D., J-R. Brisson, V. Varma, M. B. Perry. 1996. Structural analysis of the lipopolysaccharide from *Vibrio cholerae* O139. *Carbohydr. Res.* 290:43-58.

5. Fass, R., M. van de Walle, A. Shiloach, A. Joslyn, J. Kaufman, and J. Shiloach. 1991. Use of high density cultures of *Escherichia coli* for high level production of recombinant *Pseudomonas aeruginosa* exotoxin A. *Appl. Microbiol. Biotechnol.* 36:65-69.

6. Finkelstein, R. A. 1962. Vibriocidal antibody inhibition (VAI) analysis: A technique for the identification of the predominant vibriocidal antibodies in serum and for the detection and identification of *Vibrio cholerae* antigens. *J. Immunol.* 89:264-271.

7. Finkelstein, R. A. 1984. Cholera. In: *Bacterial Vaccines*, Ed. R. Germanier. Academic Press Inc. New York. pp. 107-129

8. Finkelstein, R. A., M. Boesman-Finkelstein, D. K. Sengupta, W. J. Page, C. M. Stanley, and T. E. Phillips. 1997. Colonial opacity variations among the choleragenic vibrios. *Microbiol.* 13:23-24

9. Gotschlich, E. C., M. Rey, W. R. Sanborn, R. Triau and B. Cvjetanovic. 1972. The immunological responses observed in field studies in Africa with Group A meningococcal vaccines. *Prog. in Immunobiological. Stand.* 129:485-491.

10. Gupta, R. K., D. N. Taylor, D. A. Bryla, J. B. Robbins, and S. C. Szu. 1998. Phase 1 evaluation of *Vibrio cholerae* O1, serotype Inaba, polysaccharide-cholera toxin conjugates in adult volunteers. *Infect. Immun.* 66:3095-3099.

11. Gunawardena, A., C. R. Fiore, J. A. Johnson, and C. A. Bush. 1999. Conformation of a rigid tetrasaccharide epitope in the capsular polysaccharide of *Vibrio cholerae* O139. *Biochemistry.* 38:12062-12071.

12. Hall, R. H., F. M. Khambaty, M. H. Kothary, S. P. Keasler, and B. D. Tall. 1994. *Vibrio cholerae* non-O1 serogroup associated with cholera gravis genetically and physiologically resembles O1 El Tor cholera strains. *Infect. Immun.* 62:3859-3863.

13. Hoge, Ch. W., L. Bodhidatta, P. Echeverria, M. Deesuwan, and P. Kitporka. 1996. Epidemiologic study of *Vibrio cholerae* O1 and O139 in Thailand: at the advancing edge of the eight pandemic. *Am. J. Epidemiol.* 143:263-268.

14. Inman, J. K., H. M. Dintzis. 1969. The derivatization of cross-linked polyacrylamide beads. Controlled induction of functional groups for the purpose of special biochemical absorbents. *Biochem.* 4:4074-4080.

15. Johnson, V. G., and P. J. Nicholls. 1994. Histidine 21 does not play a major role in diphtheria toxin catalysis. *J. Biol. Chem.* 269:4349-4354.

16. Johnson, J. A., A. Joseph, and J. G. Morris, Jr. 1995. Capsular polysaccharide-protein conjugate vaccines against *Vibrio cholerae* O139 Bengal. *Bull Inst. Pasteur.* 93:285-290.

17. Johnson, G., J. Osek, A. M. Svennerholm, and J. Holmgren. 1996. Immune mechanisms and protective antigens of *Vibrio cholerae* serogroup O139 as a basis for vaccine development. *Infect. Immun.* 64:3778-3786.

18. Keleti, G., and W. Lederer. 1974. *Handbook of micromethods for the biological Sciences:* 3,6-*dideoxyhexoses*, pp. 57-58. Van Nostrand Reinhold Company. New York, Cincinnati, Atlanta, Dallas, San Francisco, London, Toronto, Melbourne.

19. Knirel, Y. A., L. Paredes, P-E. Jansson, A. Weintraub, G. Widmal and M. J. Albert. 1995. Structure of the capsular polysaccharide of *Vibrio cholerae* O139 synonym Bengal containing D-galactose-4,5-cyclophosphate. *Eur. J. Biochem.* 232:391-396.

20. Kohn, J., M. Wilchek. 1983. 1-Cyano-4-dimethylaminopyridinium tetrafluoroborate as a cyanylating agent for the covalent attachment of ligand to polysaccharide resins. *FEBS Letts.* 154:209-210.

21. Konadu, E., J. Shiloach, D. A. Bryla, J. B. Robbins, S. C. Szu. 1996. Synthesis, characterization and immunological properties in mice of conjugates composed of detoxified lipopolysaccharide of *Salmonella paratyphi* A bound to tetanus toxoid, with emphasis on the role of O-acetyls. *Infect. Immun.* 64:2709-2715.

22. Kossaczka, Z., S. Bystricky, D. A. Bryla, J. Shiloach, J. B. Robbins, and S. C. Szu. 1997. Synthesis and immunological properties of Vi and Di-O-acetyl pectin protein conjugates with adipic acid dihydrazide as the linker. *Infect. Immun.* 65:2088-2093.

23. Lees, A., B. L. Nelson, and J. J. Mond. 1996. Activation of soluble polysaccharides with 1-cyano-4-dimethylaminopyridinium tetrafluoroborate for use in protein-polysaccharide conjugate vaccines and immunological reagents. *Vaccine* 14:190-198.

24. Levine, M. M., D. R. Nalin, J. P. Craig, D. Hoover, E. J. Bergquist, D. Waterman, H. P. Holley, R. B. Hornick, N. P. Pierce and J. P. Libonati. 1979. Immunity of cholera in man:

Relative role of antibacterial versus antitoxic immunity. *Trans. Royal Soc. Trop. Med. Hyg.* 73:3-9.

25. Losonsky, G. A., Y. Lim, P. Motamedi, L. Comstock, J. A. Johnson, J. G. Morris, Jr., C. O. Tacket, J. B. Kaper, and M. M. Levine. 1997. Vibriocidal antibody responses in North American volunteers exposed to wild-type or vaccine *Vibrio cholerae* O139: Specificity and relevance to immunity. *Clin. Diagnos. Lab. Immunol.* 4:264-269.

26. Meno, Y., M. K. Waldor, J. J. Mekalanos, and K. Amako. 1998. Morphological and physical characterization of the capsular layer of *Vibrio cholerae* O139. *Arch. Microbiol.* 170:339-344.

27. Merritt, C. B., and R. B. Sack. 1970. Sensitivity of agglutinating and vibriocidal antibodies to 2-mercaptoethanol in human cholera. *J. Infect. Dis.* 121:S25-S30.

28. Morris, J. G., G. E. Losonsky, J. A. Johnson, C. O. Tacket, J. P. Nataro, P. Panigrahi, and M. M. Levin. 1995. Clinical and immunologic characteristics of *Vibrio cholerae* O139 Bengal infection in North American volunteers. *J. Infect. Dis.* 171:903-908.

29. Mosley, W. H. 1969. The role of immunity in cholera. A review of epidemiological and serological studies. *Tex. Rep. Biol. Med.* 27(Suppl 1):227-241.

30. Nandy, R. K., M. J. Albert, A. C. Ghose. 1996. Serum antibacterial and antitoxin responses in clinical cholera caused by *Vibrio cholerae* O139 Bengal and evaluation of their importance in protection. *Vaccine* 14:1137-1142.

31. Nandy, R. K., S. Mukhopadhyay, A. N. Ghosh, and A. C. Ghose. 1999. Antibodies to the truncated (short) form of "O" polysaccharides (TFOP) of *Vibrio cholerae* O139 lipopolysaccharides protect mice against experimental cholera and such protection is mediated by inhibition of intestinal colonization of vibrios. *Vaccine.* 17:2844-2852.

32. Neoh, S. H., and D. Rowley. 1980. The antigens of *Vibrio cholerae* involved in the vibriocidal action of antibody and complement. *J. Infect. Dis.* 121:505-513.

33. Pike, R. M., and C. H. Chandler. 1971. Serological properties of G and M antibodies to the somatic antigen of *Vibrio cholerae* during the course of immunization of rabbits. *Infect. Immun.* 6:803-809.

34. Plikaytis, B. D., P. F. Holder, and G. M. Carlone. 1996. Program ELISA for Windows. User's Manual 12, Version 1.00. Centers for Disease Control, Atlanta, Ga.

35. Preston, L. M., Q. Xu, J. A. Johnson, A. Joseph, D. R. Maneval Jr, K. Hussain, G. P. Reddy, C. A. Bush, and J. G. Morris Jr. 1995. Preliminary structure determination of the capsular polysaccharide of *Vibrio cholerae* O139 Bengal A11837. *J. Bacteriol.* 177:835-838.

36. Robbins, J. B., R. Schneerson and S. C. Szu. 1995. Perspective: Hypothesis: Serum IgG antibody is sufficient to confer protection against infectious diseases by inactivating the inoculum. *J. Infect. Dis.* 171:1387-1398.

37. Schneerson, R., O. Barrera, A. Sutton, and J. B. Robbins. 1980. Preparation, characterization and immunogenicity of *Haemophilus influenzae* type b polysaccharide-protein conjugates. *J. Exp. Med.* 152:361-376.

38. Sengupta, D. K., M. Boesman-Finkelstein, and R. A. Finkelstein. 1996. Antibody against the capsule of *Vibrio cholerae* O139 protects against experimental challenge. *Infect. Immun.* 64:343-345.

39. Szu, S. C., R. Gupta, and J. B. Robbins. 1994. Induction of serum vibriocidal antibodies by O-specific polysaccharide-protein conjugate vaccines for prevention of cholera. p. 381-394. In I. K. Wachsmuth, P. A. Blake and O Olsvik (ed). *Vibrio cholerae*. American Society for Microbiology, Washington D.C.

40. Tacket, C. O., G. E. Losonsky, J. P. Nataro, L. Comstock, J. Michalski, R. Edelman, J. B. Kaper, M. M. Levine. 1995. Initial clinical studies of CVD 112 *Vibrio cholerae* O139 live oral vaccine: safety and efficacy against experimental challenge. *J. Infect. Dis.,* 172:883-886.

41. U.S. Department of Health and Human Services, Public Health Service, Food and Drug Administration Guideline on Validation of the Limulus Amebocyte Lysate Test As an End-product Endotoxin Test for Human and Animal Parenteral Drugs, Biological Products, and Medical Devices. 1987.

42. Waldor, K. M., J. J. Mekalanos. 1994. Emergence of a new cholera pandemic: molecular analysis of virulence determinants in *Vibrio cholerae* O139 and development of a live vaccine prototype. *J. Infect. Dis.,* 170:278-283.

43. Waldor, M. K., R. Colwell, and J. J. Mekalanos. 1994. The *Vibrio cholerae* O139 serogroup antigen includes an O-antigen capsular and lipopolysaccharide virulence determinants. *Proc. Natl. Acad. Sci (USA)* 91:11388-11392

44. Wasserman, S. G., G. A. Losonsky, F. Noriega, C. O. Tacket, E. Castaneda and M. M. Levine. 1994. Kinetics of the vibriocidal antibody response to live oral cholera vaccines. *Vaccine.* 11:1000-1003.

45. Weintraub, A., G. Widmalm, P. -E. Jansson, M. Jansson, K. Hultenby, and M. J. Albert. 1994. *Vibrio cholerae* O139 Bengal possesses a capsular polysaccharide which may confer increased virulence. *Microb. Pathog.* 16:235-241.

46. Oscarson, S., U. Tedebark, and D. Tuerk. 1997. Synthesis of colitose-containing oligosaccharide structures found in polysaccharides from *Vibrio cholerae* O139 synonym Bengal using thioglycoside donors. *Carbohydr. Res.* 299:159-164.

47. Kossacza, Z., J. Shiloach, V. Johnson, D. N. Taylor, R. A. Finkelstein, J. B. Robbins, and S. C. Szu. 2000. *Vibrio cholerae* O139 Conjugate Vaccines: Synthesis and Immunogenicity in Mice of *V. cholerae* O139 Capsular Polysaccharide Conjugates with Recombinant Diphtheria Toxin Mutant in Mice. *Infect. Immun.* 68:5037-5043.

48. For reviews, see:
(a) J. B. Robbins, R. Schneerson, S. Szu, V. Pozsgay, In: *Vaccinia, vaccinations and vaccinology: Jenner, Pasteur and their successors* (Ed.: S. Plotkin, B. Fantini), Elsevier, Paris, 1996, p. 135-143.
(b) R. K. Sood, A. Fattom, V. Pavliak, R. B. Naso, *Drug Discovery Today* 1996, 1:381-387.
(c) A. Fattom, *Adv. Expt. Med. Biol.* 1995, 383:131-139.
(d) U. B. S. Sǿrenson, *Danish Med. Bull.* 1995, 42:47-53.
(e) H. J. Jennings, R. K. Sood, In *Neoglycoconjugates. Preparation and Applications* (Eds. Y. C. Lee, R. T. Lee), Academic Press, New York, 1994, pp. 325-371.
(f) W. Egan, *Ann. Rep. Med. Chem.* 1993, 28:257-265.
(g) P. R. Paradiso, K. Dermody, S. Pillai, *Vaccine Research* 1993, 2:239-248.
(h) H. J. Jennings, *Curr. Top. Microbiol. Immunol.* 1990, 150:97-127.

49. For the development of this concept, see:
(a) K. Landsteiner, *The specificity of serological reactions*, Harvard University Press, Cambridge, 1970.
(b) W. F. Goebel, O. T. Avery, *J. Exp. Med.* 1929, 50:521-531.

50. J. B. Robbins, R. Schneerson, P. Anderson, D. H. Smith, *J. Am Med. Assoc.* 1996, 276:1181-1185.

51. For example:
(a) D. Cohen, S. Ashkenazi, M. S. Green, M. Gdalevich, G. Robin, R. Slepon, M. Yavzori, N. Orr, C. Block, Y. Ashkenazi, J. Schemer, D. N. Taylor, T. L. Hale, J. D. Sadoff, D. Pavliakova, R. Schneerson, J. B. Robbins, *Lancet,* 1997, 349:155-0159.

(b) D. Cohen, S. Ashkenazi, M. S. Green, Y. Lerman, R. Slepon, G. Robin, N. Orr, D. N. Taylor, J. C. Sadoff, C. Chu, J. Shiloach, R. Schneerson, J. B. Robbins, *Infect. Immun.* 1997, 64:4074-4077.

52. Fournier, J. M., S. Villeneuve. 1998. Actualite du cholera et problematique vaccinale [Cholera update and vaccination problems]. *Med. Trop.* 58 (2 Suppl): 32-35.

53. V. P. Bondre, V. B. Sinha, B. S. Srivastava. 1998. Evaluation of different subcellular fractions of *Vibrio cholerae* O139 in protection to challenge in experimental cholera. *FEMS Imm. Med. Micro.* 19:323-329.

54. Fattom, A., C. Lue, S. C. Szu, J. Mestecky, G. Schiffman, D. A. Bryla, W. F. Vann, D. Watson, L. M. Kimzey, J. B. Robbins, and R. Schneerson. 1990. Serum antibody response in adult volunteers elicited by injection of *Streptococcus pneumoniae* type 12F polysaccharide alone or conjugated to diphtheria toxoid. *Infect. Immun.,* 58:2309-2312.

55. Devi, S. J., J. B. Robbins and R. Schneerson. 1991. Antibodies to poly[(2→8)-α-N-acetylneuraminic acid] are elicited by immunization of mice with *Escherichia coli* K92 conjugates: Potential vaccines for groups B and C meningococci and *E. coli. Proc. Natl. Acad. Sci. USA* 88:7175-7179.

56. Szu, S. C., X. Li, R. Schneerson, J. H. Vickers, D. Bryla, and J. B. Robbins. 1989. Comparative immunogenicities of Vi polysaccharide-protein conjugates composed of cholera toxin or its B subunit as a carrier bound to high- or lower-molecular-weight Vi. *Infect. Immun.* 57:3823-3827.

57. Szu, S. C., X. Li, A. L. Stone, and J. B. Robbins. 1991. Relation between structure and immunologic properties of the Vi capsular polysaccharide. *Infect. Immun.* 59:4555-4561.

58. Szu, S. C., A. L. Stone, J. D. Robbins, R. Schneerson, and J. B. Robbins. 1987. Vi capsular polysaccharide-protein conjugates for prevention of typhoid fever. *J. Exp. Med.* 166:1510-1524.

59. Szu, S. C., D. N. Taylor, A. C. Trofa, J. D. Clements, J. Shiloach, J. C. Sadoff, D. A. Bryla and J. B. Robbins. 1994. Laboratory and preliminary clinical characterization of Vi capsular polysaccharide-protein conjugate vaccines. *Infect. Immun.* 62:4440-4444

60. C. Chu. B. Liu, D. Watson, S. Szu, D. Bryla, J. Shiloach, R. Schneerson and J. B. Robbins. 1991. Preparation, Characterization, and Immunogenicity of Conjugates Composed of the O-Specific Polysaccharide of *Shigella dysenteriae* Type 1 (Shiga's Bacillus) Bound to Tetanus Toxoid. *Infect. Immun.,* 59:4450-4458.

61. Robbins, J. B.; R. Schneerson, S. C. Szu, D. A. Bryla, F. Y. Lin, E. C. Gotschlich. 1998. Standardization may suffice for licensure of conjugate vaccines. *Dev. Biol. Stand.* 95:161-167.

62. Favre, D., S. J. Cryz Jr., J. -F. Viret. 1996. Construction and Characterization of a Potential Live Oral Carrier-Based Vaccine against *Vibrio Cholerae* O139. *Infect. Immun.* 64:3565-3570.

63. Shafer D. E., B. Toll, R. F. Schuman, B. L. Nelson, J. J. Mond, A. Lees 2000. Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides. *Vaccine* 18:1273-1281

64. Hermanson, G. T. 1996. *Bioconjugate techniques*, Academic Press, San Diego.

Modifications of the above described modes for carrying out the invention that are obvious to those of skill in the fields of immunology, protein chemistry, medicine, and related fields are intended to be within the scope of the following claims.

Every reference cited hereinabove is hereby incorporated by reference in its entirety.

We claim:

1. A conjugate molecule, comprising the capsular polysaccharide of *Vibrio cholerae* O139, covalently bound with an adipic acid dihydrazide linker to a carrier protein, wherein the carrier protein is a recombinant diphtheria toxin comprising CRMH21G, wherein the conjugate comprises a polysaccharide to protein ratio of about 0.76 and elicits serum antibodies vibriocidal to *Vibrio cholerae* O139.

2. A pharmaceutical composition comprising the conjugate molecule of claim 1, in a physiologically acceptable carrier.

3. A method of eliciting serum antibodies in a mammal that have vibriocidal activity against *Vibrio cholerae* O139, comprising conjugating a capsular polysaccharide of *Vibrio cholerae* O139 covalently bound with an adipic acid dihydrazide linker to a carrier protein, in which the carrier protein is a recombinant diphtheria toxin comprising CRMH21G, by about 0.02 M 1-ethyl-3-(3-dimethylaminopropyl) carbodiimide (EDC), thereby preparing a conjugate molecule comprising a polysaccharide to protein ratio (weight/weight) of about 0.76;

administering to the mammal at least three doses of a therapeutically effective amount of the conjugate molecule, thereby eliciting serum antibodies comprising anti-diphtheria toxin IgG at a concentration of about 1050 ELISA units/milliliter of serum.

4. A method of immunizing a mammal against *Vibrio cholerae* O139, comprising administering to the mammal a therapeutically effective amount of an isolated antibody or fragment thereof, wherein the antibody is elicited by the method of claim 3.

5. The method of claim 3, wherein the mammal is a human.

6. The method of claim 3, wherein the conjugate molecule is administered at a dose of about 1 microgram to about 100 milligrams of *Vibrio cholerae* O139 capsular polysaccharide.

7. The method of claim 4, wherein the mammal is a human.

8. The method of claim 4, wherein the isolated antibody is administered at a dose of about 1 mg/kg of body weight to about 10 mg/kg of body weight.

* * * * *